United States Patent
Sugiyama

(10) Patent No.: US 10,500,257 B2
(45) Date of Patent: Dec. 10, 2019

(54) METHOD OF SELECTING WT1 VACCINE ADAPTIVE PATIENT

(75) Inventor: Haruo Sugiyama, Minoo (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 587 days.

(21) Appl. No.: 10/562,486

(22) PCT Filed: Jun. 25, 2004

(86) PCT No.: PCT/JP2004/009378
§ 371 (c)(1),
(2), (4) Date: Dec. 27, 2005

(87) PCT Pub. No.: WO2005/001117
PCT Pub. Date: Jan. 6, 2005

(65) Prior Publication Data
US 2007/0128207 A1     Jun. 7, 2007

(30) Foreign Application Priority Data

Jun. 27, 2003 (JP) ................................. 2003-184436
Mar. 12, 2004 (JP) ................................. 2004-070497

(51) Int. Cl.
*A61K 39/00* (2006.01)
*G01N 33/50* (2006.01)

(52) U.S. Cl.
CPC ........... *A61K 39/00* (2013.01); *G01N 33/505* (2013.01); *G01N 33/5091* (2013.01)

(58) Field of Classification Search
None
See application file for complete search history.

(56) References Cited

U.S. PATENT DOCUMENTS

| | | |
|---|---|---|
| 4,923,799 A | 5/1990 | Mak |
| 5,512,478 A | 4/1996 | Orser et al. |
| 6,013,444 A | 1/2000 | Dau et al. |
| 6,225,051 B1 | 5/2001 | Sugiyama |
| 6,582,908 B2 | 6/2003 | Fodor et al. |
| 2002/0131960 A1 | 4/2002 | Sadelain et al. |
| 2004/0097703 A1 | 5/2004 | Sugiyama |
| 2004/0247609 A1 | 12/2004 | Sugiyama |
| 2005/0002951 A1 | 1/2005 | Sugiyama et al. |
| 2005/0260222 A1 | 11/2005 | Gupta et al. |
| 2005/0266014 A1 | 12/2005 | Sugiyama et al. |
| 2006/0035291 A1 | 2/2006 | Itoh et al. |
| 2007/0082860 A1 | 4/2007 | Sugiyama et al. |
| 2007/0238099 A1 | 10/2007 | Cohen et al. |
| 2008/0070835 A1 | 3/2008 | Sugiyama |
| 2008/0152631 A1 | 6/2008 | Sugiyama |
| 2009/0099090 A1 | 4/2009 | Sugiyama et al. |
| 2010/0190163 A1 | 7/2010 | Sugiyama |
| 2014/0255941 A1 | 9/2014 | Sugiyama |
| 2014/0315735 A1 | 10/2014 | Sugiyama |
| 2014/0315758 A1 | 10/2014 | Sugiyama |

FOREIGN PATENT DOCUMENTS

| | | | |
|---|---|---|---|
| CN | 101668853 A | 3/2010 | |
| EP | 1410804 A1 | 4/2004 | |
| EP | 1 447 091 | 8/2004 | |
| EP | 1473564 | 11/2004 | |
| EP | 1536009 | 6/2005 | |
| EP | 1550453 | 6/2005 | |
| EP | 1640458 A1 | 3/2006 | |
| EP | 2 116 596 A1 | 11/2009 | |
| JP | 2001-517958 | 10/2001 | |
| JP | 2002-515243 | 5/2002 | |
| JP | 2002-525099 | 8/2002 | |
| JP | 2003-500004 | 1/2003 | |
| JP | 2009-278927 A | 12/2009 | |
| KR | 2002-0013503 A | 2/2002 | |
| WO | 93-04695 A1 | 3/1993 | |
| WO | WO 98/54223 A2 | 12/1998 | |
| WO | WO 99/14371 A1 | 3/1999 | |
| WO | WO 99/27957 | 6/1999 | |
| WO | 99-60119 A2 | 11/1999 | |
| WO | 00-18795 A2 | 4/2000 | |
| WO | WO-0018795 A2 * | 4/2000 | ......... C07K 14/4748 |
| WO | 00-26249 A1 | 5/2000 | |

(Continued)

OTHER PUBLICATIONS

Nagai et al., "Increased Activated Human T cell Lymphotropic Virus Type I (HTLV-1) Tax11-19 Specific Memory and Effector CD8+ Cells in Patients with HTLV-1-Associated Myelopathy/Tropical Spastic Paraparesis: Correlation with HTLV-1 Provirus Load", J. of Infectious Disease, 183:197-205, 2001.*

Gotoh et al., "Development of HLA-A2402/Kb Transgenic Mice", Int. J. Cancer: 100, 565-570 (2002).*

Brenchley et al., Clin Exp Immunol 2002; 130:431-440 (Year: 2002).*

Pittet et al., Trends in Immunology vol. 23 No. 7, 2002, pp. 325-328 (Year: 2002).*

Powell et al. J Immunother 2004; 27:36-47. (Year: 2004).*

Lee et al., Nature Medicine, vol. 5, No. 6, 1999. (Year: 1999).*

Yu et al., J Clin Invest. Aug. 1, 2002; 110(3): 289-294. (Year: 2002).*

(Continued)

*Primary Examiner* — Zachary S Skelding
(74) *Attorney, Agent, or Firm* — Oblon, McClelland, Maier & Neustadt, L.L.P.

(57) ABSTRACT

A method of selecting patients highly responsive to WT1 vaccine and a therapeutic method for treating cancer involving said method of selection are provided, which method of selecting patients highly responsive to WT1 vaccine comprises: (a) isolating a biological sample containing CTL precursor cells from a test subject; (b) measuring the existence frequency or amount of WT1-specific CTL precursor cells in the biological sample of (a); and (c) deciding whether or not the measured value of (b) is high by comparison with that of healthy subject, and evaluating the responsiveness to WT1 vaccine.

16 Claims, 1 Drawing Sheet
Specification includes a Sequence Listing.

(56) References Cited

FOREIGN PATENT DOCUMENTS

| WO | 00/50641 A1 | 8/2000 |
|---|---|---|
| WO | 02/28414 | 4/2002 |
| WO | WO 02/079253 A1 | 10/2002 |
| WO | 03/002142 | 1/2003 |
| WO | 03025569 | 3/2003 |
| WO | WO 03/025569 A1 | 3/2003 |
| WO | 03/028757 | 4/2003 |
| WO | 03/037060 | 5/2003 |
| WO | WO 2003/59155 | 7/2003 |
| WO | 03/106682 | 12/2003 |
| WO | WO 2004/063706 A2 | 7/2004 |
| WO | 2005-053603 A2 | 6/2005 |
| WO | WO 2005/116074 | 8/2005 |
| WO | WO 2006/064176 A1 | 6/2006 |
| WO | WO 2008/026927 A2 | 3/2008 |
| WO | 2008/108257 A1 | 9/2008 |

OTHER PUBLICATIONS

Meidenbauer et al., Methods. Oct. 2003;31(2):160-71. (Year: 2003).*
Andersen et al., Tissue Antigens. Jun. 2000;55(6):519-31. (Year: 2000).*
Katayoun Rezvani, et al., "Functional leukemia-associated antigen-specific memory CD8$_+$ T cells exist in healthy individuals and in patients with chronic myelogenous leukemia before and after sterm cell transplantation" Blood, Oct. 15, 2003, vol. 102. No. 8, Jun. 26, 2003,pp. 2892-2900, XP-002474847, ISSN:0006-4971, version published online on Jun. 26, 2003, pp. 1-35.
Y.Oka, et al., "WT1 as Novel Target Antigen for Cancer Immunotherapy", Current Cancer Drug Targets, vol. 2, 2002, pp. 45-54, XP008089881.
Yoshihiro Oka, et al., "Cancer Immunotherapy Targeting Wilms' Tumor Gene WT1 Product [1]", Journal of Immunology (Baltimore, MD.: 1950), Feb. 15, 2000, vol. 164, No. 4, pp. 1873-1880, XP000890067, ISSN: 0022-1767.
Ivan M. Borrello, et al., "Cancer Vaccines for Hematologic Malignancies", Cancer Control: Journal of the Moffitt Cancer Center Mar.-Apr. 2002, vol. 9, No. 2, Mar. 2002, pp. 138-151, XP002475149, ISSN: 1073-2748.
Y. Maeda, et al., "Detection of peptide-specific CTL-precursors in peripheral blood lymphocytes of cancer patients", British Journal of Cancer, Sep. 23, 2002, vol. 87, No. 7, pp. 796-804, XP002475150, ISSN: 0007-0920.
Akihiro Tsuboi, et al., "WT1 Peptide-Based Immunotherapy for Patients with Lung Cancer: Report of Two Cases", Microbiology and Immunology 2004, vol. 48, No. 3, pp. 175-184, XP002391404, ISSN: 0385-5600.
Altman, John D. et al., "Phenotypic Analysis of Antigen-Specific T Lymphocytes", Science, vol. 274, pp. 94-96, 1996.
Menke, A. L. et al., "The Wilms' Tumor 1 Gene: Oncogene or Tumor Suppressor Gene?", International Review of Cytology, vol. 181, pp. 151-212, 1998.
Oertli, Daniel, et al.,"Rapid Induction of Specific Cytotoxic T Lymphocytes Against Melanoma-Associated Antigens by a Recombinant Baccinia Virus Vector Expressing Multiple Immunodominant Epitopes and Costimulatory Molecules In Vivo", Human Gene Therapy, vol. 13, pp. 569-575, 2002.
Lau, Roy et al., "Phase I Trial of Intravenous Peptide-Pulsed Dendritic Cells in Patients With Metastatic Melanoma", vol. 24, No. 1, pp. 66-78, 2001.
Moller, P. et al., "Vaccination with IL-7 gene-modified autologous melanoma cells can enhance the anti-melanoma lytic activity in peripheral blood of patients with a good clinical performances status: a clinical phase I study", British Journal of Cancer, vol. 77, No. 11, pp. 1907-1916, 1998.
Kruse, Niels et al.,"Quantification of cytokine mRNA expression by RT PCR in samples of previously frozen blood", Journal of Immunological Methods, vol. 210, pp. 195-203, 1997.
Czerkinsky, Cecil et al., "Reverse ELISPOT assay for clonal analysis of Cytokine production, I. Enumeration of gamma-interferon-secreting cells", Journal of Immunological Methods, vol. 110, pp. 29-36, 1998.
Sugiyama, Haruo, "Cancer Immunotherapy Targeting WT1 Protein", International Journal of Hematology, vol. 76, pp. 127-132, 2002.
Gessler, Manfred et al., "Homozygous deletion in Wilms tumours of a zinc-finger gene identified by chromosome jumping", Nature, vol. 343, pp. 774-778, 1990.
Call, Katherine M. et al., "Isolation and Characterization of a Zinc Finger Polypeptide Gene at the Human Chromosome 11 Wilms' Tumor Locus", Cell, vol. 60, pp. 509-520, 1990.
Akihiro Tsuboi, et al., "Enhanced induction of human WT1-specific cytotoxic T lymphocytes with a 9-mer WT1 peptide modified at HLA-A*2402-binding residues", Cancer Immunol Immnother, (2002), vol. 51 pp. 614-620.
Yoshihiro Oka, et al., "Cancer Immunotherapy Targeting Wilms'Tumor Gene WT1 Product", The Journal of Immunology, vol. 164, pp. 1873-1880.
Y. Maeda, et al., "Detection of peptide-specific CTL-precursors in peripheral blood lymphocytes of cancer patients", British Journal of Cancer, (2002) vol. 87, pp. 796-804.
Hideki Ohminami, et al., "HLA class I-restricted lysis of leukemia cells by a CD8$^+$ cytotoxic T-lymphocyte clone specific for WT1 peptide", Blood, Jan. 1, 2002, vol. 95, No. 1, pp. 286-293.
Akihiro Tsuboi, et al. "Enhanced induction of human WT1-speific cytotoxic T lymphocytes with a 9-mer WT1 peptide modified at HLA-A*2402-binding residues", (1996), vol. 274, pp. 94-96, XP003016309, (CAPLUS-abstract).
Office Action and Search Report dated Nov. 4, 2014, issued in Chinese patent application No. 201280042412.0 with English translation.
Kato,T., et al., "Analysis of Accumulated T Cell Clonotypes in Patients with Systemic Lupus Erythematosus", Arthritis & Rheumatism, vol. 43, No. 12, pp. 2712-2721, (Dec. 2000).
Valmori, D., et al., "Vaccination with a Melan-A Peptide Selects an Oligoclonal T Cell Population with Increased Functional Avidity and Tumor Reactivity", The Journal of Immunology, vol. 168, pp. 4231-4240, (2002).
Dietrich, P., et al., "Melanoma Patients Respond to a Cytotoxic T Lymphocyte-defined Self-Peptide with Diverse and Nonoverlapping T-Cell Receptor Repertoires", Cancer Research, vol. 61, pp. 2047-2054, (Mar. 1, 2001).
Coulie, P. G., et al., "A monoclonal cytolytic T-lymphocyte response observed in a melanoma patient vaccinated with a tumor-specific antigenic peptide encoded by gene MAGE-3", vol. 98, No. 18, pp. 10290-10295, (Aug. 28, 2001).
Ochsenreither et al, ""Wilms Tumor Protein 1" (WT1) Peptide Vaccination-induced Complete Remission in a Patient With Acute Myeloid Leukemia Is Accompanied by the Emergence of a Predominant T-cell Clone Both in Blood and Bone Marrow" Journal of Immunotherapy, vol. 34, No. 1, XP009181179, Jan. 2011, pp. 85-91.
Ochsenreither et al, "Wilms' tumor protein 1 (WT1) peptide vaccination in AML patients: predominant TCR CDR3β sequence associated with remission in one patient is detectable in other vaccinated patients" Cancer Immunol Immunother, vol. 61, XP35018866, 2012, pp. 313-322.
M. Nagai et al.—"Increased Activated Human T Cell Lymphotropic Virus Type I (HTLV-I0 Tax 11-19-Specific Memory and Effector CD8+ Cells in Patients with HTLV-I-Associated Myelopathy/Tropical Spastic Paraparesis: Correlation with THLV-I Provirus Load", The Journal of Infectious Diseases, vol. 183, pp. 197-205.
Pinilla-Ibarz et al.—"Improved human T-cell response against synthetic HLA-0201 analog peptides derived from the WT1-oncoprotein" Leukemia, 29: 2026-2033(2006).
Genbank Accession No. AAM92197 "T-cell receptor beta chain variable region, partial [*Homo sapiens*]" published Aug. 10, 2002.
T. Schumacher—"T-Cell Receptor Gene Therapy" Nature Reviews Immunology, Vo. 2, Issue 7, Jul. 2002, pp. 512-519.
K. Willenbrock—"Analysis of T-Cell Subpopulations in T-Cell Non-Hodgkin's Lymphoma of Angioimmunoblastic Lymphadenopathy with Dysproteinemia Type by Single Target Gene Amplification

(56) References Cited

OTHER PUBLICATIONS of T Cell Receptor-β Gene Rearrangements," American Journal of Pathology vol. 158, No. 5, May 2001, pp. 1851-1857.
Kruger et al.—"Lessons to be learned from primary renal cell carcinomas: novel tumor antigens and HLA ligands for immunotherapy," Cancer Immunol. Immunother. 54, pp. 826-836 (2005).
Robinson et al.—"IMGT/HLA Database—a sequence database for the human major histocompatibility complex", Tissue Antigens, 55: 280-287 (2000).
Godelaine, D., et al., "Polyclonal CTL Responses Observed in Melanoma Patients Vaccinated with Dendritic Cells Pulsed with a MAGE-3.A1 Peptide", The Journal of Immunology, vol. 171, pp. 4893-4897, (2003).
Mandruzzato, S., et al., "Large and Dissimilar Repertoire of Melan-A/MART-1-Specific CTL in Metastatic Lesions and Blood of a Melanoma Patient", The Journal of Immunology, vol. 169, pp. 4017-4024, (2002).
Hirschhorn et al. "A comprehensive review of genetic association studies", Genetics in Medicine, Mar./Apr. 2002, vol. 4, No. 2, pp. 45-61.
Ioannidis et al. "Replication validity of genetic association studies", Nature Genetics, vol. 29, Nov. 2001, pp. 306-309.
O'Keefe et al. "Molecular Analysis of TCR Clonotypes in LGL: A Clonal Model for Polyclonal Responses", The Journal of Immunology, 2004, vol. 172, No. 3, pp. 1960-1969.
Abbey et al., "Expression of T-cell receptor genes during early T-cell development", Immunology and Cell Biology, 2008, 86, pp. 166-174.
Farina et al. "Conserved TCR usage by HLA-Cw*1601-restricted T cell clones recognizing melanoma antigens", International Immunology, 1996, vol. 8, No. 9, pp. 1463-1466.
Oka et al. "Wilms Tumor Gene Peptide-Based Immunotherapy for Patients with Overt Leukemia from Myelodysplastic Syndrome (MDS) or MDS with Myelofibrosis", International Journal of Hematology, 2003, vol. 78, No. 1, pp. 56-61.
Coppage et al. "In vitro generation of tumor specific T cells that recognize a shared antigen of AML: Molecular characterization of TCR genes", Leukemia Research 31, 2007, pp. 195-202.
Zhou et al. Database Genbank, 2003, XP-002569162.
Rezvani et al. "T-Cell Responses Directed against Multiple HLA-A*0201-Restricted Epitopes Derived from Wilms' Tumor 1 Protein in Patients with Leukemia and Healthy Donors: Identification, Quantification, and Characterization", Clinical Cancer Research Dec. 15, 2005, vol. 11, No. 24, pp. 8799-8807.
Halapi et al. "T cell receptor usage in malignant diseases", Springer Seminars in Immunopathology (1999), vol. 21, No. 1, pp. 19-35 XO-002568655.
Xue et al. "Elimination of human leukemia cells in NOD/SCID mice by WT1-TCR gene-transduced human T cells", Blood, 2005, 106, pp. 3062-3067.
Armstrong et al. "Conformational changes and flexibility in T-cell receptor recognition of peptide-MHC complexes", Biochem J., 2008, 415, pp. 183-196.
T cell receptor beta chain variable region [*Homo sapiens*], GenBank: ABF14434.1 (2006) 1 page.
T cell receptor beta chain [*Homo sapiens*], GenBank: BAC01035.1 (2002) 2 pages.
"AICAR transformylase PurH [Helicobacter hepaticus ATCC 51449", GenBank: AAP77080.1 (Mar. 11, 2010) 1 page.
"*Homo sapiens* T cell receptor beta chain (BV16S1) mRNA, partial cds", GenBank: AF317601.1 (2001) 1 page.
"T-cell receptor beta-chain [*Homo sapiens*]", GenBank CAC06601.1 (2001) 1 page.
"T cell receptor beta chain [*Homo sapiens*]", GenBank: AAG15764.1 (2000) 1 page.
"T cell receptor beta chain, partial [*Homo sapiens*]", GenBank: AAC52008.1 (1998) 1 page.

Borbulevych et al.—"Structures of native and affinity-enhanced WT1 epitopes bound to HLA-A*0201: implications for WT1-based cancer therapeutics", *Mol Immunol.* Sep. 2010 47(15), pp. 2519-2524.
Kasprowicz et al.—"A Highly Restricted T-Cell Receptor Dominates the CD8+ T-Cell Response to Parovirus B19 infection in HLA-A*2402-Positive Individuals", Journal of Virology, vol. 80, No. 13, Jul. 2006, pp. 6697-6701.
Office Action dated Jul. 18, 2017, in Japanese patent application No. 2015-151065 (w/English translation).
Final Office Action dated Feb. 9, 2017, in U.S. Appl. No. 14/184,979.
Office Action dated Feb. 9, 2017, in Chinese patent application No. 201280042412.0 (w/English translation).
Sommer and Tautz, "Minimal homology requirements for PCR primers", Nucleic Acids Research, 1989, vol. 17, No. 16 , p. 6749.
Final Office Action dated May 10, 2017, in U.S. Appl. No. 12/529,701.
Final Office Action dated May 9, 2017, in U.S. Appl. No. 14/184,816.
Sugiyama H, Wilms' tumor gene WT1: its oncogenic function and clinical application;, Feb. 1, 2001, International Journal of Hematology, Elsevier Science Publishers, NL, pp. 177-187.
Herr E. et al., "Frequency analysis of tumor-reactive cytotoxic T lymphocytes in peripheral blood of a melanoma patient vaccinated with autologous tumor cells." Cancer Immunology, Immunotherapy; CII Aug. 1994 LNKD-Pubmed:8044834, vol. 39, No. 2, Aug. 1994, pp. 93-99.
Oka Y, et al., "Induction of WT1 (Wilm's tumor gene)-specific cytotoxic T lymphocytes by WT1 peptide vaccine and the resultant cancer regression", Proceedings of the National Academy of Sciences, National Academy of Schicens, Washington, DC; US, vol. 101, No. 38, Sep. 21, 2004, pp. 13885-13890.
Whiteside T. L., "Monitoring of antigen-specific cytolytic T lymphocytes in cancer patients receiving immunotherapy." Climncal and Diagnostic Laboratory Immunology May 2000, pp. 327-332.
Extended European Search Report dated Oct. 31, 2011 in Application No. 11154327.8-1223/2338509.
Extended European Search Report dated Jul. 1, 2011 in Application No. 11154325.2-1223/2343083.
Non-final Office Action dated Nov. 2, 2016, in U.S. Appl. No. 14/184,816.
Combined Canadian Office Action and Search Report dated Mar. 29, 2018 in Canadian Patent Application No. 2,679,045, 6 pages.
Kurokawa, T., et al., "Induction and Clonal Expansion of Tumor-Specific Cytotoxic T Lymphocytes from Renal Cell Carcinoma Patients after Stimulation with Autologous Dendritic Cells Loaded with Tumor Cells", International Journal of Cancer, vol. 91, 2001, pp. 749-756 with cover page.
Hodges, E., et al., "Diagnostic Role of Tests for T Cell Receptor (TRC) Genes", J Clin. Pathol., vol. 56, 2003, pp. 1-11.
Final Office Action dated Jan. 20, 2017, in U.S. Appl. No. 14/129,695.
Non-Final Office Action dated Jan. 27, 2017, in U.S. Appl. No. 14/687,569.
Office Action dated Aug. 22, 2017, in Japanese patent application No. 2016-193222 (w/English translation).
Office Action dated Aug. 24, 2017, in U.S. Appl. No. 14/687,628.
U.S. Non-Final Office Action dated Mar. 7, 2018, in copending U.S. Appl. No. 14/687,569.
Katayoun Rezvani, et al., Blood, Oct. 15, 2003, vol. 102, No. 8, Jun. 26, 2003, pp. 2892-2900.
Office Action dated Nov. 1, 2017, in Chinese patent application No. 201310258589.0 (w/English translation).
Li Yanqiu, et al, "The feature of CDR3 sequence of TCR Vβ 21 oligoclonal T cells in CML", *Immunological Journal*, 2000, vol. 16, No. 3, pp. 189-192 (w/English abstract).
Office Action dated Dec. 5, 2016, in European Patent Application No. 12 803 980.7.
Final Office Action dated Dec. 2, 2016 in U.S. Appl. No. 14/687,628.
Office Action dated Feb. 1, 2012 in corr. U.S. Appl. No. 12/529,701, filed Mar. 26, 2010.
Office Action dated Aug. 8, 2012 in corr. U.S. Appl. No. 12/529,701, filed Mar. 26, 2010.
Office Action dated Aug. 22, 2013 in corr. U.S. Appl. No. 12/529,701, filed Mar. 26, 2010.

(56) References Cited

OTHER PUBLICATIONS

Office Action dated Feb. 14, 2014 in corr. U.S. Appl. No. 12/529,701, filed Mar. 26, 2010.
Office Action dated May 15, 2015 in corr. U.S. Appl. No. 14/129,695, filed Dec. 27, 2013.
Office Action dated Aug. 20, 2015 in corr. U.S. Appl. No. 14/184,816, Feb. 20, 2014.
Office Action dated Nov. 16, 2015 in corr. U.S. Appl. No. 14/687,628, filed Apr. 15, 2015.
Office Action dated Jan. 7, 2016 in corr. U.S. Appl. No. 14/129,695, filed Dec. 27, 2013.
Office Action dated May 12, 2016 in corr. U.S. Appl. No. 14/687,628, filed Apr. 15, 2015.
Office Action dated Aug. 8, 2016 in corr. U.S. Appl. No. 14/687,569, filed Apr. 15, 2015.
Office Action dated Nov. 27, 2012 in corr. Australian Patent Application No. 2008222061, filed Feb. 28, 2008.
Office Action dated May 31, 2013 in corr. Australian Patent Application No. 2008222061, filed Feb. 28, 2008.
Office Action dated Oct. 23, 2013 in corr. Australian Patent Application No. 2008222061, filed Feb. 28, 2008.
Office Action dated Dec. 20, 2013 in corr. Australian Patent Application No. 2008222061, filed Feb. 28, 2008.
Patent Examination Report dated Jun. 4, 2015 in corr. Australian Patent Application No. 2013206501, filed Jun. 24, 2013.
Patent Examination Report dated Jun. 4, 2015 in corr. Australian Patent Application No. 2013270605, filed Dec. 13, 2013.
Second Office Action and Search Report dated Jul. 16, 2015, in corr. Chinese Patent Application No. 201280042412.0, filed Jun. 20, 2012 (w/ English translation).
Decision on Rejection dated Feb. 14, 2016 in corr. Chinese Patent Application No. 201280042412.0, filed Jun. 20, 2012 (w/ English translation).
Extended European Search Report dated Mar. 5, 2010 in corr. European Patent Application No. 08720964.9, filed Feb. 28, 2008.
European Office Action dated May 10, 2011 in corr. European Patent Application No. 08720964.9, filed Feb. 28, 2008.
Office Action dated Oct. 15, 2012 in corr. European Patent Application No. 08720964.9, filed Feb. 28, 2008.
Office Action dated May 6, 2014 issued in corr. European Patent Application No. 08720964.9, filed Feb. 28, 2008.
Partial Supplementary Search Report dated Nov. 27, 2014, issued in corr. European Patent Application No. 12803980.7, filed Jun. 20, 2012.
Partial Supplementary Search Report dated Jan. 5, 2015, issued in corr. European Patent Application No. 12803980.7, filed Jun. 20, 2012.
Extended European Search Report dated Mar. 18, 2015 in European application No. 14192034.8, filed Feb. 28, 2008.
Supplementary European Search Report and Opinion dated May 12, 2015 in corr. European Patent Application No. 12803980.7, filed Jun. 20, 2012.
Summons dated May 2, 2016 in corr. European Patent Application No. 08720964.9, filed Feb. 28, 2008.
International Search Report dated Aug. 7, 2012 in corr. International Patent Application No. PCT/JP2012/065707, filed Jun. 20, 2012 (w/ partial English translation).
International Preliminary Report on Patentability dated Jan. 16, 2014 in corr. International Patent Application No. PCT/JP2012/065707, filed Jun. 20, 2012 (English translation only).
Office Action dated Apr. 16, 2013 in corr. Japanese Patent Application No. 2009-502541, filed Feb. 28, 2008 (w/ partial English translation).
Office Action dated Feb. 4, 2014 in corr. Japanese Patent Application No. 2009-502541, filed Feb. 28, 2008 (w/ partial English translation).
Office Action dated Apr. 26, 2016 in corr. Japanese Patent Application No. 2013-0522787, filed Jun. 20, 2012 (w/ English translation).
Office Action dated Jul. 12, 2016 in corr. Japanese Patent Application No. 2015-0151065, filed Jul. 30, 2015 (w/ partial English translation).
Office Action dated Mar. 24, 2016 in corr. Korean Patent Application No. 10-2015-7023123, filed Feb. 28, 2008 (w/ partial English translation).
Correspondence RE Mexican Office Action dated Nov. 15, 2012 in corr. Mexican Patent Application No. 2009/009589, filed Feb. 28, 2008.
M. Yasukawa, "Immunogenetherapy for Leukemia by T-cell Receptor Gene Transfer", Hematology & Oncology, vol. 51, No. 3, Sep. 2005, pp. 320-326 (w/ partial English translation).
Oka et al., "Cancer Immunotherapy Targeting Wilms' Tumor Gene WT1 Product1", The Journal of Immunology, vol. 164, 2000, pp. 1873-1880.
Kimura et al, "Clinical and Immunologic Evaluation of Dendritic Cell-Based Immunotherapy in Combination With Gemcitabine and/or S-1 in Patients With Advanced Pancreatic Carcinoma", *Pancreas*, 2012, vol. 41, No. 2, pp. 195-205.
Murao et al, "High frequencies of less differentiated and more proliferative WT1-specific CD8+ T cells in bone marrow in tumor-bearing patients: An important role of bone marrow as a secondary lymphoid organ", *Cancer Science*, 2010, vol. 101, No. 4, pp. 848-854.
Van Tendeloo et al, "Induction of complete and molecular remissions in acute myeloid leukemia by Wilms' tumor 1 antigen-targeted dendritic cell vaccination", *PNAS*, 2010, vol. 107, No. 31, pp. 13824-13829.
Office Action dated May 29, 2018 in Japanese Patent Application No. 2016-193222 with partial English translation, 6 pages.
Kawakami, Y. "Recent progress in the development of immunotherapy for melanoma", Skin Cancer, vol. 19, No. 1, 2004, pp. 25-33 (with English Abstract).
Partial European Search Report dated Jan. 24, 2019 in European Patent Application No. 18193944.8, 18 pages.
Extended European Search Report dated May 16, 2019 in Patent Application No. 19150097.4, 16 pages.
U.S. Pat. No. 8,735,357, May 27, 2014, 2004/0247609 A1, Sugiyama, Dec. 2004.
U.S. Pat. No. 7,030,212, Apr. 18, 2006, Sugiyama, et al.
U.S. Appl. No. 10/471,835, filed May 20, 2004, 2004/0097703 A1, Sugiyama.
U.S. Appl. No. 10/490,865, filed Jan. 6, 2005, 2005/0002951 A1, Sugiyama, et al.
U.S. Pat. No. 7,420,034, Sep. 2, 2008, 2007/0082860 A1, Sugiyama, et al, Apr. 2007.
U.S. Pat. No. 7,342,092, Mar. 11, 2008, 2007/0036808 A1, Sugiyama, Feb. 2007.
U.S. Pat. No. 7,378,384, May 27, 2008, 2006/0205667 A1, Sugiyama, et al, Sep. 2006.
U.S. Pat. No. 7,390,871, Jun. 24, 2008, 2005/0266014 A1, Sugiyama, et al, Dec. 2005.
U.S. Pat. No. 7,608,685, Oct. 27, 2009, Sugiyama, et al.
U.S. Appl. No. 10/541,821, filed Sep. 28, 2006, 2006/0217297 A1, Sugiyama, et al.
U.S. Pat. No. 7,517,950, Apr. 14, 2009, 2006/0093615 A1, Sugiyama, et al, May 2006.
U.S. Pat. No. 7,666,985, Feb. 23, 2010, 2009/0099090 A1, Sugiyama, et al.
U.S. Appl. No. 11/953,281, filed Oct. 22, 2009, 2009/0263409 A1, Sugiyama.
U.S. Pat. No. 7,807,792, Oct. 5, 2010, 2009/0281043 A1, Sugiyama, et al.
U.S. Pat. No. 8,105,604, Jan. 31, 2012, 2009/0325886 A1, Sugiyama.
U.S. Pat. No. 8,388,975, Mar. 5, 2013, 2010/0062013 A1, Sugiyama.
U.S. Appl. No. 10/578,183, filed Mar. 20, 2008, 2008/0070835 A1, Sugiyama.
U.S. Pat. No. 7,622,119, Nov. 24, 2009, 2008/0152631 A1, Sugiyama.
U.S. Pat. No. 8,759,483, Jun. 24, 2014, 2010/0292160 A1, Sugiyama.
U.S. Pat. No. 8,653,038, Feb. 18, 2014, 2011/0098233 A1, Sugiyama.
U.S. Appl. No. 12/449,765, filed Sep. 30, 2010, 2010/0247556 A1, Sugiyama.

(56) References Cited

OTHER PUBLICATIONS

U.S. Appl. No. 12/529,701, filed Jul. 29, 2010, 2010/0190163 A1, Sugiyama.
U.S. Pat. No. 7,939,637, May 10, 2011, 2010/0062010 A1, Nishihara et al.
U.S. Pat. No. 9,403,886, Aug. 2, 2016, 2009/0143291 A1, Sugiyama, et al, Jun. 2009.
Hideki Ohminami, et al., "HLA class I-restricted lysis of leukemia cells by a CD+ cytotoxic T-lymphocyte clone specific for WT1 peptide", Blood, Jan. 1, 2002, vol. 95, No. 1, pp. 286-293.

\* cited by examiner

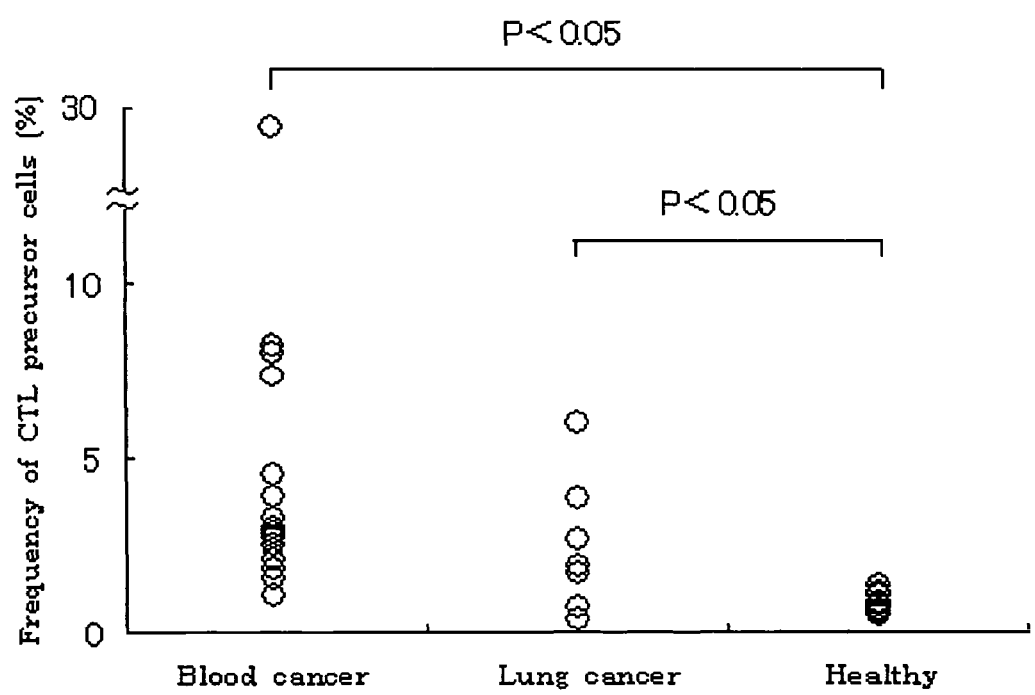

SEQUENCE LISTING

```
<160> NUMBER OF SEQ ID NOS: 22

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175
```

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Gly Ser Ser Ser
            245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
            325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
        370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
            405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Met Thr Trp Asn Gln Met Asn Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Cys Tyr Thr Trp Asn Gln Met Asn Leu
1               5

```
<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Arg Met Phe Pro Asn Ala Pro Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Arg Tyr Pro Ser Cys Gln Lys Lys Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Ser Tyr Thr Trp Asn Gln Met Asn Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Ala Tyr Thr Trp Asn Gln Met Asn Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Gly Tyr Thr Trp Asn Gln Met Asn Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Arg Tyr Thr Trp Asn Gln Met Asn Leu
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Lys Tyr Thr Trp Asn Gln Met Asn Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 11

Arg Tyr Phe Pro Asn Ala Pro Tyr Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Arg Tyr Pro Gly Val Ala Pro Thr Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Ala Tyr Leu Pro Ala Val Pro Ser Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Asn Tyr Met Asn Leu Gly Ala Thr Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Arg Val Pro Gly Val Ala Pro Thr Leu
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Arg Tyr Pro Ser Ser Gln Lys Lys Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Arg Tyr Pro Ser Ala Gln Lys Lys Phe
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Arg Tyr Pro Ser Gly Gln Lys Lys Phe
1               5

<210> SEQ ID NO 19
<211> LENGTH: 40
<212> TYPE: DNA
<213> ORGANISM: Artificial Sequence
<220> FEATURE:
<223> OTHER INFORMATION: Synthetic DNA

<400> SEQUENCE: 19
ccatgggcag ccattctatg cgctattttt ctacctccgt                              40

<210> SEQ ID NO 20
<211> LENGTH: 45
<212> TYPE: DNA
<213> ORGANISM: Artificial Sequence
<220> FEATURE:
<223> OTHER INFORMATION: Reverse Primer

<400> SEQUENCE: 20
ggatcctggc tcccatctca gggtgagggg cttgggcaga ccctc                       45

<210> SEQ ID NO 21
<211> LENGTH: 30
<212> TYPE: DNA
<213> ORGANISM: Artificial Sequence
<220> FEATURE:
<223> OTHER INFORMATION: Synthetic DNA

<400> SEQUENCE: 21
catatgatcc agcgtacccc gaaaattcag                                        30

<210> SEQ ID NO 22
<211> LENGTH: 30
<212> TYPE: DNA
<213> ORGANISM: Artificial Sequence
<220> FEATURE:
```

```
<223> OTHER INFORMATION: Reverse Primer

<400> SEQUENCE: 22
ggatccttac atgtctcgat cccacttaac                                          30
```

METHOD OF SELECTING WT1 VACCINE ADAPTIVE PATIENT

TECHNICAL FIELD

The present invention relates to a method of selecting patients highly responsive to WT1 vaccine and a therapeutic method for treating cancer involving said method of selection. More particularly, the present invention relates to a method of selecting patients highly responsive to WT1 vaccine on the basis of the frequency of WT1-specific CTL precursors as an indicator, and the like.

BACKGROUND ART

The WT1 gene (Wilms' tumor gene 1) has been identified as one of causative genes of Wilms' tumor that is a childhood renal tumor (Cell 60: 509, 1990, Nature 343: 774, 1990). WT1 gene encodes the transcription factor WT1, and WT1 plays an important role in many processes such as proliferation, differentiation and apoptosis of cells, and development of tissues (Int. Rev. Cytol. 181: 151, 1998). The WT1 gene was originally defined as a tumor suppressor gene. However, subsequent studies revealed that WT1 gene is highly expressed in leukemia and various solid cancers including lung cancer and breast cancer, and thus, indicating that WT1 gene rather exerts an oncogenic function promoting cancer growth. In addition, it was demonstrated that stimulation in vitro of peripheral blood mononuclear cells, which cells are positive to HLA-A*0201 or HLA-A*2402, with WT1-derived peptides induces the peptide-specific cytotoxic T-lymphocytes (CTLs), and the CTLs kill leukemia or solid tumor cells endogenously expressing WT1. These results demonstrated that WT1 is a promising target molecule of cancer immunotherapy (Int. J. Hematol 76: 127, 2002).

There have been known methods for determining in vitro antigen peptide-specific CTLs, including HLA monomer method, HLA dimer method and HLA tetramer method (Science 274: 94, 1996), HLA pentamer method and ELISPOT method (J. Immunol. Methods 110: 29, 1988), realtime RT-PCR technique (J. Immunol. Methods 210: 195, 1997), limiting dilution method (Br. J. Cancer 77: 1907, 1998), and the like. HLA-tetramer is prepared by biotinylating a complex (HLA monomer) formed by association of HLA α-chain and β2-microglobulin with a peptide, and allowing the monomer to bind to fluorescence-labeled avidin for tetramerization. The frequencies of CTLs can be measured by staining peptide-specific CTLs with HLA tetramers and analyzing by flow cytometry. Measurement of CTL frequencies by HLA monomer method, HLA dimer method and HLA pentamer method can be carried out on the basis of the same principle.

CTLs not stimulated with vaccine are referred to as "CTL precursor cells". It is considered that the higher the frequency of existence of CTL precursor cells specific for a given cancer antigen, the more efficiently induced specific CTLs can be, when the said antigen is administered as a cancer vaccine, which makes it easier to attain clinical response of cancer vaccine therapy. In other words, if a patient showing high frequency of existence regarding CTL precursor cells specific for a given caner antigen is selected prior to vaccination, it would be possible to treat more effectively by the use of said cancer antigen.

Frequency of CTL precursor cells were measured using HLA tetramer and peripheral blood mononuclear cells (PBMC) of melanoma patients and reported in several papers; however, they show that the frequency of CTL precursor cells specific for tumor antigen peptide is low (J. Immunother. 24: 66, 2001, Hum. Gene. Ther. 13: 569, 2002). From these results, it has been regarded that the frequency of existence of CTL precursor cells specific for antigen is generally low and that it is difficult to select patients suitable for a cancer vaccine on the basis of the frequency of CTL precursor cells as an indicator.

DISCLOSURE OF INVENTION

The purpose of the present invention is to provide a method of selecting a patient highly responsive to WT1 vaccine on the basis of the frequency of WT1-specific CTL precursor cells as an indicator, and the like.

The present inventor prepared an HLA tetramer using a tumor antigen peptide derived from WT1, and used the resultant tetramer in the measurement of frequency of CTL precursor cells in patients of hematopoietic malignancy or lung cancer before administration of vaccine. It was surprisingly found that CTL precursor cells (WT1-specific CTL precursor cells) exist in high frequency than that hitherto known compared to healthy individuals. This result revealed that it is possible to select patients highly responsive to WT1 vaccine or to identify a target molecule of WT1 vaccine on the basis of the frequency of WT1-specific CTL precursor cells as an indicator, as far as tumor antigen WT1 concerns. Also, since patients having various cancers showed high frequency of WT1-specific CTL precursor cells, it became clear that diagnosis of cancer can be done on the basis of the frequency of WT1-specific CTL precursor cells as an indicator.

The present inventor then sorted WT1-specific CTL precursor cells finely regarding function, and found that, in particular, effector-type CTL precursor cell (hereinafter, it may be simply referred to as "effector cell") exists in higher proportion among CTL precursor cells. This result indicated that selection of patients highly responsive to WT1 vaccine or diagnosis of cancer can also be carried out on the basis of the frequency of WT1-specific CTL precursor cells of effector type as an indicator.

In addition, the present inventor measured the frequency of WT1-specific CTLs in patients undergoing treatment with a tumor antigen peptide ("WT1 peptide") derived from WT1 and found that the therapeutic effect is correlated with the increase of CTL frequency after administration relative to that obtained before administration.

The present invention has been established on the basis of the findings above.

Thus, the present invention provides the followings:
(1) A method of selecting a patient highly responsive to WT1 vaccine, comprising the following steps (a), (b) and (c):
   (a) isolating a biological sample containing CTL precursor cells from a test subject;
   (b) measuring the existence frequency or amount of WT1-specific CTL precursor cells in the biological sample of (a); and
   (c) deciding whether or not the measured value of (b) is high by comparison with that of healthy subject, and evaluating the responsiveness to WT1 vaccine.
(2) The method of selection as described in (1) above, wherein the measurement of the existence frequency or amount of WT1-specific CTL precursor cells is carried out by any one of HLA monomer method, HLA dimer method, HLA tetramer method, HLA pentamer method, ELISPOT method, realtime RT-PCR technique and limiting dilution method.

(3) The method of selection as described in (2) above, wherein the measurement is carried out by HLA tetramer method.

(4) The method of selection as described in (3) above, which comprises the following steps (a), (b), (c) and (d):
(a) isolating a biological sample containing CTL precursor cells from a test subject;
(b) bringing an HLA tetramer comprising a WT1-derived tumor antigen peptide contact with the biological sample of (a);
(c) measuring the existence frequency or amount of WT1-specific CTL precursor cells bound to the HLA tetramer; and
(d) deciding whether or not the measured value of (c) is high by comparison with that of healthy subject, and evaluating the responsiveness to WT1 vaccine.

(5) The method of selection as described in (4) above, wherein the step (c) in (4) is carried out by measuring the proportion of HLA tetramer-bound cells among CD8-positive or CD8/CD3-positive CTL precursor cells.

(6) The method of selection as described in (4) or (5) above, wherein the HLA antigen as a component of HLA tetramer is an HLA-A24 antigen or an HLA-A2 antigen.

(7) The method of selection as described in any one of (4) to (6) above, wherein the WT1-derived tumor antigen peptide is selected from the following peptides:

```
Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu  (SEQ ID NO: 4)
and

Arg Tyr Pro Ser Cys Gln Lys Lys Phe. (SEQ ID NO: 5)
```

(8) The method of selection as described in any one of (1) to (7) above, which is carried out using flow cytometry.

(9) The method of selection as described in (1) to (8) above, wherein the responsiveness to WT1 vaccine is evaluated using as an indicator that the existence frequency or amount of WT1-specific CTL precursor cells is 1.5 times or higher compared to that of healthy subject.

(10) The method of selection as described in (1) above, wherein the CTL precursor cells are CTL precursor cells of effector type.

(11) The method of selection as described in (10) above, which uses any one of HLA monomer method, HLA dimer method, HLA tetramer method, HLA pentamer method, ELISPOT method, realtime RT-PCR technique and limiting dilution method in the measurement of the existence frequency or amount of WT1-specific CTL precursor cells of effector type.

(12) The method of selection as described in (11) above, which uses the HLA tetramer method.

(13) The method of selection as described in (12) above, which comprises the following steps (a), (b), (c) and (d):
(a) isolating a biological sample containing CTL precursor cells from a test subject;
(b) bringing an HLA tetramer comprising a WT1-derived tumor antigen peptide, an anti-CD8 antibody, an anti-CD45RA antibody and an anti-CD27 antibody contact with the biological sample of (a);
(c) measuring the proportion of CD45RA-postive and CD27-negative CTL precursor cells of effector type among CTL precursor cells which are positive for CD8 or CD8/CD3 and positive for binding to HLA tetramer; and
(d) deciding whether or not the measured result of (c) is high by comparison with that of healthy subject, and evaluating the responsiveness to WT1 vaccine.

(14) The method of selection as described in (13) above, wherein the HLA antigen as a component of HLA tetramer is an HLA-A24 antigen or an HLA-A2 antigen.

(15) The method of selection as described in (13) or (14) above, wherein the WT1-derived tumor antigen peptide is selected from the following peptides:

```
Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu  (SEQ ID NO: 4)
and

Arg Tyr Pro Ser Cys Gln Lys Lys Phe. (SEQ ID NO: 5)
```

(16) The method of selection as described in any one of (10) to (15) above, which is carried out using flow cytometry.

(17) A method of diagnosing cancer, comprising the following steps (a), (b) and (c):
(a) isolating a biological sample containing CTL precursor cells from a test subject;
(b) measuring the existence frequency or amount of WT1-specific CTL precursor cells in the biological sample of (a); and
(c) deciding whether or not the measured result of (b) is high by comparison with that of healthy subject, and evaluating whether the test subject has cancer.

(18) The method of diagnosis as described in (17) above, wherein the measurement of the existence frequency or amount of WT1-specific CTL precursor cells is carried out by any one of HLA monomer method, HLA dimer method, HLA tetramer method, HLA pentamer method, ELISPOT method, realtime RT-PCR technique and limiting dilution method.

(19) The method of diagnosis as described in (18) above, wherein the measurement is carried out by HLA tetramer method.

(20) The method of diagnosis as described in (19) above, which comprises the following steps (a), (b), (c) and (d):
(a) isolating a biological sample containing CTL precursor cells from a test subject;
(b) bringing an HLA tetramer comprising a WT1-derived tumor antigen peptide contact with the biological sample of (a);
(c) measuring the existence frequency or amount of WT1-specific CTL precursor cells bound to the HLA tetramer; and
(d) deciding whether or not the measured result of (c) is high by comparison with that of healthy subject, and evaluating whether the test subject has cancer.

(21) The method of diagnosis as described in (20) above, wherein the step (c) in (20) is carried out by measuring the proportion of HLA tetramer-bound cells among CD8-positive or CD8/CD3-positive CTL precursor cells.

(22) The method of diagnosis as described in (20) or (21) above, wherein the HLA antigen as a component of HLA tetramer is an HLA-A24 antigen or an HLA-A2 antigen.

(23) The method of diagnosis as described in any one of (20) to (22) above, wherein the WT1-derived tumor antigen peptide is selected from the following peptides:

Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu (SEQ ID NO: 4) and

Arg Tyr Pro Ser Cys Gln Lys Lys Phe. (SEQ ID NO: 5)

(24) The method of diagnosis as described in any one of (17) to (23) above, which is carried out using flow cytometry.
(25) The method of diagnosis as described in any one of (17) to (24) above, wherein cancer is diagnosed using as an indicator that the existence frequency or amount of WT1-specific CTL precursor cells is 1.5 times or higher compared to that of healthy subject.
(26) The method of diagnosis as described in (17) above, wherein the CTL precursor cells are CTL precursor cells of effector type.
(27) The method of diagnosis as described in (26) above, which uses any one of HLA monomer method, HLA dimer method, HLA tetramer method, HLA pentamer method, ELISPOT method, realtime RT-PCR technique and limiting dilution method in the measurement of the existence frequency or amount of WT1-specific CTL precursor cells of effector type.
(28) The method of diagnosis as described in (27) above, which uses the HLA tetramer method.
(29) The method of diagnosis as described in (28) above, which comprises the following steps (a), (b), (c) and (d):
(a) isolating a biological sample containing CTL precursor cells from a test subject;
(b) bringing an HLA tetramer comprising a WT1-derived tumor antigen peptide, an anti-CD8 antibody, an anti-CD45RA antibody and an anti-CD27 antibody contact with the biological sample of (a);
(c) measuring the proportion of CD45RA-postive and CD27-negative CTL precursor cells of effector type among CTL precursor cells which are positive for CD8 or CD8/CD3 and positive for binding to HLA tetramer; and
(d) deciding whether or not the measured value of (c) is high by comparison with that of healthy subject, and evaluating whether the test subject has cancer.
(30) The method of diagnosis as described in (29) above, wherein the HLA antigen as a component of HLA tetramer is an HLA-A24 antigen or an HLA-A2 antigen.
(31) The method of diagnosis as described in (29) or (30) above, wherein the WT1-derived tumor antigen peptide is selected from the following peptides:

Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu (SEQ ID NO: 4) and

Arg Tyr Pro Ser Cys Gln Lys Lys Phe. (SEQ ID NO: 5)

(32) The method of diagnosis as described in any one of (26) to (31) above, which is carried out using flow cytometry.
(33) A method of identifying a target molecule of WT1 vaccine said molecule being peculiar to a patient, comprising the following steps (a), (b), (c) and (d):
(a) isolating a biological sample containing CTL precursor cells from a test patient;
(b) applying each of plural target molecules of WT1 vaccine to the biological sample of (a);
(c) measuring the existence frequency or amount of WT1-specific CTL precursor cells in the respective biological samples of (b) and comparing the results with each other; and
(d) identifying a target molecule of WT1 vaccine effective to the test patient on the basis of the results obtained in (c).
(34) The method of identification as described in (33) above, wherein the measurement of the existence frequency or amount of WT1-specific CTL precursor cells is carried out by any one of HLA monomer method, HLA dimer method, HLA tetramer method, HLA pentamer method, ELISPOT method, realtime RT-PCR technique and limiting dilution method.
(35) The method of identification as described in (34) above, wherein the measurement is carried out by HLA tetramer method.
(36) The method of identification as described in (35) above, which comprises the following steps (a), (b), (c) and (d):
(a) isolating a biological sample containing CTL precursor cells from a test patient;
(b) bringing each of plural HLA tetramers comprising different WT1-derived tumor antigen peptides contact with the biological sample of (a);
(c) measuring the existence frequency or amount of WT1-specific CTL precursor cells bound to the respective HLA tetramers, and comparing the results with each other; and
(d) identifying a WT1-derived tumor antigen peptide effective to the test patient on the basis of the results obtained in (c).
(37) The method of identification as described in (36) above, wherein the step (c) in (36) is carried out by measuring the proportion of HLA tetramer-bound cells among CD8-positive or CD8/CD3-positive CTL precursor cells.
(38) The method of identification as described in (36) or (37) above, wherein the HLA antigen as a component of HLA tetramer is an HLA-A24 antigen or an HLA-A2 antigen.
(39) The method of identification as described in any one of (36) to (38) above, wherein the WT1-derived tumor antigen peptide is selected from the following peptides:

Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu (SEQ ID NO: 4) and

Arg Tyr Pro Ser Cys Gln Lys Lys Phe. (SEQ ID NO: 5)

(40) The method of identification as described in any one of (33) to (39) above, which is carried out using flow cytometry.
(41) A clinical diagnostic agent for selecting a patient highly responsive to WT1 vaccine, which comprises as an ingredient an HLA monomer, an HLA dimer, an HLA tetramer or an HLA pentamer each containing a WT1-derived tumor antigen peptide.
(42) The clinical diagnostic agent as described in (41) above, wherein the HLA antigen as a component of an HLA monomer, an HLA dimer, an HLA tetramer or an HLA pentamer is an HLA-A24 antigen or an HLA-A2 antigen.
(43) The clinical diagnostic agent as described in (41) or (42) above, wherein the WT1-derived tumor antigen peptide is selected from the following peptides:

```
Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu  (SEQ ID NO: 4)
and

Arg Tyr Pro Ser Cys Gln Lys Lys Phe. (SEQ ID NO: 5)
```

(44) A kit comprising a clinical diagnostic agent as described in any one of (41) to (43) above.

(45) A pharmaceutical composition for treating cancer in a given patient, which comprises a target molecule identified by the method of identification of a target molecule of WT1 vaccine said molecule being peculiar to the patient as described in any one of (33) to (40) above.

(46) A diagnostic agent for cancer, which comprises as an ingredient an HLA monomer, an HLA dimer, an HLA tetramer or an HLA pentamer each containing a WT1-derived tumor antigen peptide.

(47) The diagnostic agent as described in (46) above, wherein the HLA antigen as a component of an HLA monomer, an HLA dimer, an HLA tetramer or an HLA pentamer is an HLA-A24 antigen or an HLA-A2 antigen.

(48) The diagnostic agent as described in (46) or (47) above, wherein the WT1-derived tumor antigen peptide is selected from the following peptides:

```
Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu  (SEQ ID NO: 4)
and

Arg Tyr Pro Ser Cys Gln Lys Lys Phe. (SEQ ID NO: 5)
```

(49) A kit which comprises a diagnostic agent as described in any one of (46) to (48) above.

(50) A method of determining the suitability of a patient for WT1 vaccine, comprising the following steps (a), (b) and (c):
  (a) isolating a biological sample containing CTLs from a patient after WT1 vaccine administration;
  (b) measuring the existence frequency or amount of WT1-specific CTLs in the biological sample of (a);
  (c) deciding whether or not the measured value of (b) is high by comparison with that of biological sample obtained before WT1 vaccine administration, and evaluating whether the patient is suitable for WT1 vaccine therapy.

(51) The method of determination as described in (50) above, wherein the measurement of the existence frequency or amount of WT1-specific CTLs is carried out by any one of HLA monomer method, HLA dimer method, HLA tetramer method, HLA pentamer method, ELISPOT method, realtime RT-PCR technique and limiting dilution method.

(52) The method of determination as described in (51) above, wherein the measurement is carried out by HLA tetramer method.

(53) The method of determination as described in (52) above, which comprises the following steps (a), (b), (c) and (d):
  (a) isolating a biological sample containing CTLs from a patient after WT1 vaccine administration;
  (b) bringing an HLA tetramer comprising a WT1-derived tumor antigen peptide contact with the biological sample of (a);
  (c) measuring the existence frequency or amount of WT1-specific CTLs bound to the HLA tetramer; and
  (d) deciding whether or not the measured value of (c) is high by comparison with that of biological sample obtained before WT1 vaccine administration, and evaluating whether the patient is suitable for WT1 vaccine therapy.

(54) The method of determination as described in (53) above, wherein the step (c) in (53) is carried out by measuring the proportion of HLA tetramer-bound cells among CD8-positive or CD8/CD3-positive CTLs.

(55) The method of determination as described in (53) or (54) above, wherein the HLA antigen as a component of HLA tetramer is an HLA-A24 antigen or an HLA-A2 antigen.

(56) The method of determination as described in any one of (53) to (55) above, wherein the WT1-derived tumor antigen peptide is selected from the following peptides:

```
Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu  (SEQ ID NO: 4)
and

Arg Tyr Pro Ser Cys Gln Lys Lys Phe. (SEQ ID NO: 5)
```

(57) The method of determination as described in any one of (50) to (56) above, which is carried out using flow cytometry.

(58) The method of determination as described in any one of (50) to (57) above, wherein the suitability for WT1 vaccine therapy is evaluated using as an indicator that the existence frequency or amount of WT1-specific CTLs is 1.5 times or higher compared to that in the sample obtained before administration.

(59) A clinical diagnostic agent for determining the suitability for WT1 vaccine which comprises as an ingredient an HLA monomer, an HLA dimer, an HLA tetramer or an HLA pentamer each containing a WT1-derived tumor antigen peptide.

(60) The clinical diagnostic agent as described in (59) above, wherein the HLA antigen as a component of an HLA monomer, a HLA dimer, an HLA tetramer or an HLA pentamer is an HLA-A24 antigen or an HLA-A2 antigen.

(61) The clinical diagnostic agent as described in (59) or (60) above, wherein the WT1-derived tumor antigen peptide is selected from the following peptides:

```
Cys Met Thr Trp Asn Gln Met Asn Leu, (SEQ ID NO: 2)

Cys Tyr Thr Trp Asn Gln Met Asn Leu, (SEQ ID NO: 3)

Arg Met Phe Pro Asn Ala Pro Tyr Leu  (SEQ ID NO: 4)
and

Arg Tyr Pro Ser Cys Gln Lys Lys Phe. (SEQ ID NO: 5)
```

(62) A kit comprising a clinical diagnostic agent as described in any one of (59) to (61) above.

The present invention is further related to the followings:

(63) In relation to the above-mentioned embodiment (1), a method of treating cancer in a patient, which comprises: selecting a patient highly responsive to WT1 vaccine by the following steps (a), (b) and (c):
  (a) isolating a biological sample containing CTL precursor cells from a test subject;

(b) measuring the existence frequency or amount of WT1-specific CTL precursor cells in the biological sample of (a); and
(c) deciding whether or not the measured value of (b) is high by comparison with that of healthy subject, and evaluating the responsiveness to WT1 vaccine; and
treating the selected patient with WT1 or a WT1-derived tumor antigen peptide; and
a method of treating cancer in a patient selected by a method as described in any one of (2) to (16) above.

(64) In relation to the above-mentioned embodiment (33), a method of treating cancer in a given patient, which comprises administering a target molecule of WT1 vaccine said molecule being peculiar to the patient and having been identified by a method comprising the following steps (a), (b), (c) and (d):
(a) isolating a biological sample containing CTL precursor cells from a test patient;
(b) applying each of plural target molecules of WT1 vaccine to the biological sample of (a);
(c) measuring the existence frequency or amount of WT1-specific CTL precursor cells in the respective biological samples of (b) and comparing the results with each other; and
(d) identifying a target molecule of WT1 vaccine effective to the test patient on the basis of the results obtained in (c); and
a method of treating cancer in a given patient, which comprises administering a target molecule of WT1 vaccine said molecule being peculiar to the patient and having been identified by a method as described in any one of (34) to (40) above.

(65) In relation to the above-mentioned embodiment (50), a method of treatment of cancer, which comprises treating a patient with WT1 or a WT1-derived tumor antigen peptide said patient having been evaluated to be suitable by a method of determination of suitability of a patient for WT1 vaccine, comprising the following steps (a), (b) and (c):
(a) isolating a biological sample containing CTLs from a patient after WT1 vaccine administration;
(b) measuring the existence frequency or amount of WT1-specific CTLs in the biological sample of (b);
(c) deciding whether or not the measured value of (b) is high by comparison with that of biological sample obtained before WT1 vaccine administration, and evaluating whether the patient is suitable for WT1 vaccine therapy; and
a method of treating cancer in a patient evaluated to be suitable by the method as described in any one of (51) to (58) above.

BRIEF DESCRIPTION OF DRAWINGS

FIG. 1 is a graph showing the existence frequency of WT1-specific CTL precursors in patients having cancer and healthy individuals. The vertical axis indicates the frequency of CTL precursors (precursor cells). The "blood cancer" shows the results obtained from HLA-A2402-positive patients having hematopoietic malignant tumor. The term "lung cancer" shows the results obtained from HLA-A2402-positive patients having lung cancer, and the term "healthy" the results obtained from HLA-A2402-positive healthy individuals.

BEST MODE FOR CARRYING OUT THE INVENTION

The present invention provides a method of selecting a patient highly responsive to WT1 vaccine, comprising the following steps (a), (b) and (c):
(a) isolating a biological sample containing CTL precursor cells from a test subject;
(b) measuring the existence frequency or amount of WT1-specific CTL precursor cells in the biological sample of (a); and
(c) deciding whether or not the measured value of (b) is high by comparison with that of healthy subject, and evaluating the responsiveness to WT1 vaccine, and a method of treating cancer in the patient selected by said method.

The present inventor has found that there exist CTL precursor cells (WT1-specific CTL precursor cells) in a patient before vaccine administration in high frequency than that hitherto known. Accordingly, patients highly responsive to WT1 vaccine can be selected on the basis of the amount or frequency of WT1-specific CTL precursor cells as an indicator.

The test subject in step (a) refers to a person who is suspected or diagnosed to have cancer, specifically, a person who is suspected or diagnosed to have cancer including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer. Preferred example is a person who is suspected or diagnosed to have leukemia, myelodysplastic syndrome and lung cancer.

There are no limitations regarding the biological sample isolated from a test subject in step (a) as far as it contains CTL precursor cells. Specific example includes blood, lymph fluid or cultures thereof, peripheral blood mononuclear cells (PBMCs) isolated from blood, or tissues to which T cells infiltrated, and the like. The biological sample can be used as it is, or after dilution or concentration. Preferred example is PBMC, which can be isolated by a conventional manner such as density gradient centrifugation method with Ficoll-Hypaque.

The method of measuring the existence frequency or amount of WT1-specific CTL precursor cells in step (b) can be carried out by any methods known in the art, by which the existence frequency or amount of CTL can be measured. Specific examples include HLA monomer method, HLA dimer method, HLA tetramer method, HLA pentamer method, ELISPOT method, realtime RT-PCR technique, limiting dilution method, and the like.

As herein used, the HLA tetramer method is a method wherein an antigen peptide-specific CTL is detected using an HLA tetramer prepared by biotinylating an HLA monomer (said monomer has been formed by association of an HLA antigen α-chain and a β2-microglobulin with an objective antigen peptide), and allowing to bind to fluorescently labeled avidin for tetramerization. Specifically, the amount of CTL can be determined by staining an antigen peptide-specific CTL by said HLA tetramer and analyzing by flow cytometry. Preparation of an HLA tetramer and detection of CTLs using the same are known and can be carried out according to a method, for example, described in a literature (Science 274: 94, 1996).

The HLA monomer method is a method wherein an antigen peptide-specific CTL is detected using an HLA monomer used in the preparation of HLA tetramer, which monomer is formed by association of an HLA antigen α-chain and a β2-microglobulin with an antigen peptide followed by biotinylation.

The HLA dimer method is a method wherein an antigen peptide-specific CTL is detected using an HLA dimer which is prepared by fusing an HLA antigen α-chain and an Ig (immunoglobulin, for example, IgG1), and allowing the resultant fusion to bind to β2-microglobulin and an antigen peptide (Proc. Natl. Acad. Sci. USA 90:6671-6675 (1993)). The antigen peptide-specific CTLs bound to HLA dimer can be detected by, for example, allowing labeled anti-IgG1 antibody to bind to IgG1.

The HLA pentamer method is a method that has been developed recently, wherein an antigen peptide-specific CTL is detected using a pentamer wherein five complex molecules of an HLA antigen and an antigen peptide are polymerized through Coiled-Coil domain. Since the HLA antigen-antigen peptide complex can be labeled with fluorescence or the like, the analysis can be carried out by flow cytometry or the like as is the case with HLA tetramer method (see, available via hypertext transfer protocol at URL address: www.proimmune.co.uk/).

The aforementioned HLA-monomer, dimer, tetramer and pentamer are all available by custom production from a manufacture such as ProImmune or BD Biosciences.

The ELISPOT method is a method wherein CTL in a biological sample is detected by immobilizing an antibody raised against a cytokine such as IFN-γ or GM-CSF on a plate, adding a biological sample stimulated by an intended antigen or antigen peptide, and detecting the cytokine secreted from activated CTL in the biological sample and bound to the immobilized antibody above as a spot using anti-cytokine antibody. The method of determining CTL by the ELISPOT method is known and can be carried out according to a method described in a literature (e.g., J. Immunol. Methods 110: 29, 1988).

The realtime RT-PCR method is a method wherein the frequency of CTL reactive to an objective antigen or antigen peptide is measured indirectly through the measurement of a gene encoding cytokine such as IFN-γ, GM-CSF or the like produced by activated CTL by means of RT-PCR. The method of determining CTL by the realtime RT-PCR method is known and can be carried out according to a method described in a literature (e.g., J. Immunol. Methods 210: 195, 1997).

The limiting dilution method is a method wherein the frequency of CTL is measured by plating a biological sample containing CTLs in wells at different cell densities, culturing the plate while stimulating with an objective antigen or antigen peptide, measuring the amount of cytokines or cytotoxicity produced by the activated CTLs, and determining the CTL frequency on the basis of the number of positive wells. The method of determining CTL by the limiting dilution method is known and can be carried out according to a method described in a literature (e.g., Br. J. Cancer 77: 1907, 1998).

It is possible to measure the existence frequency or amount of WT1-specific CTL precursors according to the known method for determination of CTL as mentioned above.

The evaluation of responsiveness to WT1 vaccine in step (c) can be carried out by comparing the existence frequency or amount of WT1-specific CTL precursor cells in a test subject obtained in step (b) (hereinafter, referred to as "test subject value"), with that of healthy subject (hereinafter, referred to as "healthy subject value") and deciding the difference between them. In this case, a biological material isolated and prepared from a healthy subject (blood, lymph fluid, PBMC, etc.) is needed, which can be obtained by collecting a biological sample from a subject not having cancer. As used herein, "healthy subject" means a person who has not been diagnosed to have cancer.

The comparison between the test subject values and the healthy subject values can be carried out by measuring the biological sample of a test subject and that of a healthy subject in parallel. When the parallel comparison is not conducted, comparison can also be carried out using a mean value or a statistical intermediate value of healthy subject values calculated from the healthy subject values obtained by measuring plural (at least two, preferably three or more, more preferably five or more) biological samples of a healthy subject under a constant conditions when the parallel measurement is not conducted.

The evaluation whether or not a test subject is highly responsive to WT1 vaccine can be carried out using as an indicator that the test subject value is 1.5 times or higher, preferably 2 times or higher compared to the healthy subject value. That is, when the test subject value is 1.5 times or higher, preferably, 2 times or higher than the healthy subject value, the responsiveness to WT1 vaccine is evaluated to be high. A patient evaluated to be highly responsive to WT1 vaccine is evaluated to be suitable for WT1 vaccine, in other words, it is possible to apply WT1 vaccine therapy to the patient preferably. Among the above-mentioned methods of measuring CTL, the HLA tetramer method is most preferred from the viewpoint of easiness and accuracy. Thus, in a preferred embodiment, the present invention provides a method of selecting and treating a patient highly responsive to WT1 vaccine characterized in that it uses the HLA tetramer method. As mentioned above, the HLA monomer method, HLA dimer method, and HLA pentamer method are principally the same as HLA tetramer method, and are preferred methods for measuring CTL. However, the present invention will be herein described by taking HLA tetramer method as an example.

The method of selecting and treating a patient highly responsive to WT1 vaccine by the use of HLA tetramer, specifically, comprises the following steps (a), (b), (c) and (d):

(a) isolating a biological sample containing CTL precursor cells from a test subject;

(b) bringing an HLA tetramer comprising a WT1-derived tumor antigen peptide contact with the biological sample of (a);

(c) measuring the existence frequency or amount of WT1-specific CTL precursor cells bound to the HLA tetramer; and (d) deciding whether or not the measured value of (c) is high by comparison with that of healthy subject, and evaluating the responsiveness to WT1 vaccine.

In this regard, the "biological sample" and the "test subject" in step (a) are the same as defined above.

The "HLA tetramer" used in step (b) refers to a tetramer prepared by biotinylating a complex (HLA monomer) obtained by association of an HLA antigen α-chain and a β2-microglobulin with a peptide (antigen peptide), and allowing to bind to avidin for tetramerization (Science 279: 2103-2106 (1998); and Science 274: 94-96 (1996)). The HLA tetramer is preferably labeled with fluorescence so that the CTL precursor cells can be easily sorted out or detected by a known detection measure such as flow cytometry, fluorescent microscopy, and the like. Specific examples include HLA tetramers labeled with phycoerythrin (PE), fluorescein isothiocyanate (FITC), peridinyl chlorophyll protein (PerCP), allophycocyanin (APC), phycoerythrin-texasred (also called ECD), and phycoerythrin-cyanine 5.1 (also called PC5), or the like.

The WT1-derived cancer antigen peptide used as a component of an HLA tetramer above is originated from human WT1 (Cell, 60: 509, 1990, NCBI database Accession No. XP_034418, SEQ ID NO: 1), and is able to form a complex with an HLA antigen and thereby exerting the HLA-restricted cytotoxic T cell (CTL)-inducing activity (immunogenicity).

It has been known that there are many subtypes of HLA molecule and that the amino acid sequence of tumor antigen peptide to which an HLA molecule binds obeys a certain rule (binding motif) (Immunogenetics, 41, p 178, 1995; J. Immunol., 155: p 4749, 1995). For example, the binding motif for HLA-A24 is known that, in the peptides consisting of 8-11 amino acid residues, the amino acid at position 2 is tyrosine (Tyr), phenylalanine (Phe), methionine (Met) or tryptophan (Trp), and the amino acid at the C-terminus is phenylalanine (Phe), leucine (Leu), isoleucine (Ile), tryptophan (Trp) or methionine (Met) (J. Immunol., 152, p 3913, 1994, Immunogenetics, 41, p 178, 1995, J. Immunol., 155, p 4307, 1994).

Regarding the motifs for HLA-A2, the following motifs listed in Table 1 are known (Immunogenetics, 41, p 178, 1995; J. Immunol., 155: p 4749, 1995).

TABLE 1

| HLA-A2 type | 2nd amino acid from N-terminus | amino acid at C-terminus |
| --- | --- | --- |
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

Peptide length = 8–11 amino acids

Recently, it has become possible to search peptide sequences expected to be capable of binding to HLA antigens via the internet using BIMAS software; NIH (available via hypertext transfer protocol at URL address: bimas.dcrt.nih.gov/molbio/hla_bind/). It is also possible to search for peptide sequences using BIMAS HLA peptide binding prediction analysis (J. Immunol., 152,163, 1994). Specific examples of WT1-derived peptides which have been searched and identified in such a manner are those listed in Table II-Table XLVI of WO2000/18795.

The above-mentioned WT1-derived peptides may be partially altered by substitution, deletion and/or addition of an amino acid residue(s) inclusive of addition of an amino acid residue(s) at the N- and/or C-terminus of peptide, preferably, by substitution of an amino acid residue(s). The substitution is preferably carried out with an amino acid residue available in view of the motifs mentioned above.

A WT1-derived cancer antigen peptide can be selected by subjecting the WT1-derived peptides (including variants) to a known assay for cancer antigen peptide, for example, a method described in WO02/47474 or Int. J. Cancer: 100, 565-570 (2002).

Specific examples of WT1-derived cancer antigen peptides include the following peptides.

```
Cys Met Thr Trp Asn Gln Met Asn    (SEQ ID NO: 2)
Leu

Cys Tyr Thr Trp Asn Gln Met Asn    (SEQ ID NO: 3)
Leu

Arg Met Phe Pro Asn Ala Pro Tyr    (SEQ ID NO: 4)
Leu

Arg Tyr Pro Ser Cys Gln Lys Lys    (SEQ ID NO: 5)
Phe

Ser Tyr Thr Trp Asn Gln Met Asn    (SEQ ID NO: 6)
Leu

Ala Tyr Thr Trp Asn Gln Met Asn    (SEQ ID NO: 7)
Leu

Abu Tyr Thr Trp Asn Gln Met Asn    (SEQ ID NO: 8)
Leu

Arg Tyr Thr Trp Asn Gln Met Asn    (SEQ ID NO: 9)
Leu

Lys Tyr Thr Trp Asn Gln Met Asn    (SEQ ID NO: 10)
Leu

Arg Tyr Phe Pro Asn Ala Pro Tyr    (SEQ ID NO: 11)
Leu

Arg Tyr Pro Gly Val Ala Pro Thr    (SEQ ID NO: 12)
Leu

Ala Tyr Leu Pro Ala Val Pro Ser    (SEQ ID NO: 13)
Leu

Asn Tyr Met Asn Leu Gly Ala Thr    (SEQ ID NO: 14)
Leu

Arg Val Pro Gly Val Ala Pro Thr    (SEQ ID NO: 15)
Leu

Arg Tyr Pro Ser Ser Gln Lys Lys    (SEQ ID NO: 16)
Phe

Arg Tyr Pro Ser Ala Gln Lys Lys    (SEQ ID NO: 17)
Phe

Arg Tyr Pro Ser Abu Gln Lys Lys    (SEQ ID NO: 18)
Phe
```

In the above, "Abu" refers to "α-aminoacetic acid.

Among them, the peptides set forth in SEQ ID NO: 2 and SEQ ID NO: 4 are HLA-A24 antigen- and HLA-A2 antigen-binding peptides and the other peptides set forth in SEQ ID NO: 3, 5, 6-18 are HLA-A24 antigen-binding peptides.

Preferred cancer antigen peptide can be selected from those set forth in SEQ ID NOs: 2, 3, 4 and 5 above.

An HLA tetramer may contain two or more peptides among the above-mentioned ones.

Synthesis of a peptide can be conducted according to processes generally used in the field of peptide chemistry. Such a method can be found in literatures including Peptide Synthesis, Interscience, New York, 1966; The Proteins, Vol. 2, Academic Press Inc., New York, 1976; Peptide Synthesis, Maruzen, Inc., 1975; Peptide-Gosei no Kiso to Jikken, Maruzen, Inc., 1985; and Iyakuhin no Kaihatsu (Zoku), Vol. 14, Peptide Synthesis, Hirokawa-syoten, 1991.

Also, the present invention includes peptides wherein the amino group of the N-terminal amino acid or the carboxyl group of the C-terminal amino acid of the above-described peptides is modified.

The peptides undergone such modification also fall within the scope of the present invention.

Examples of a group for the modification of amino group of the N-terminal amino acid include 1 to 3 groups selected from a $C_1$-$C_6$ alkyl group, a phenyl group, a cycloalkyl group and an acyl group, specifically, a $C_1$-$C_6$ alkanoyl group, a $C_1$-$C_6$ alkanoyl group substituted by phenyl group, a carbonyl group substituted by $C_5$-$C_7$ cycloalkyl group, a $C_1$-$C_6$ alkylsulfonyl group, a phenylsulfonyl group, a $C_2$-$C_6$ alkoxycarbonyl group, an alkoxycarbonyl group substituted by phenyl group, a carbonyl group substituted by $C_5$-$C_7$ cycloalkoxy group, and a phenoxycarbonyl group, and the like.

Examples of a group for the modification of carboxyl group of the C-terminal amino acid include an ester group and an amide group. The ester group specifically includes a $C_1$-$C_6$ alkyl ester group, a $C_0$-$C_6$ alkyl ester group substituted by phenyl group, and a $C_5$-$C_7$ cycloalkyl ester group, and the like. The amide group specifically includes an amide group, an amide group substituted by one or two $C_1$-$C_6$ alkyl groups, an amide group substituted by one or two $C_0$-$C_6$ alkyl groups that are substituted by phenyl group, and an amide group forming 5- to 7-membered azacycloalkane inclusive of nitrogen atom of amide group, and the like.

As an HLA antigen (α-chain of HLA antigen), which is a component of HLA tetramer, an HLA antigen of any subtype can be used; however, it is necessary to use an HLA antigen of the same subtype as that of the subject to be diagnosed or selected. Examples of HLA antigen includes HLA-A24 antigen such as HLA-A*2402, etc.; HLA-A2 antigen such as HLA-A*0201, -A*0204, -A*0205, -A*0206, etc.; HLA-A26 antigen such as HLA-A*2601, etc.; and HLA-A*3101, HLA-A*3303, HLA-A*1101, and the like. Specific examples include HLA-A24 antigen, HLA-A2 antigen and HLA-A26 antigen. The nucleotide and amino acid sequences of these HLA antigens are known. For example, the sequences for HLA-A24 antigen are disclosed in Cancer Res., 55: 4248-4252 (1995) and Genbank Accession No. M64740; those for HLA-A2 antigen in Genbank Accession No. M84379; and those for HLA-A26 antigen in Genbank Accession No. D14350. Accordingly, an α-chain of HLA antigen can be easily cloned on the basis of information regarding these known base sequences in a conventional manner such as PCR.

The α-chain of said HLA antigen is preferably a fragment in the soluble form to make the binding and selection of CTL easy. It is further preferred that the C-terminus of α-chain of said HLA antigen has a structure feasible for biotinylation to enable tetramerization by biotin-avidin binding, that is, has a biotin-binding portion added.

Specifically, in the case of HLA-A2402 (a kind of HLA-A24), cDNA for a recombinant soluble HLA-A*2402 α-chain which is designed to enable the specific lysine residue in the C-terminal tag to be biotinylated by BirA enzyme is prepared by PCR reaction using, as a template, an HLA-A*2402 (GenBank Acc. No. M64740) expression plasmid and, as a forward primer: 5'-CCATGGGCAGC-CATTCTATGCGCTATTTTTCTACCTCCGT-3' (SEQ ID NO: 19); and, as a reverse primer: 5'-GGATCCTGGCTC-CCATCTCAGGGTGAGGGGCTTGGGCAGACCCTC-3' (SEQ ID NO: 20).

As a β2-microglobulin which is a component of HLA tetramer, human β2-microglobulin is preferred. cDNA for said human β2-microglobulin can be prepared by PCR reaction using, as a template, a human β2-microglobulin (GenBank Acc. No. ABO21288) expression plasmid and, as a forward primer: 5'-CATATGATCCAGCGTAC-CCCGAAAATTCAG-3' (SEQ ID NO: 21); and, as a reverse primer: 5'-GGATCCTTACATGTCTCGATCCCACT-TAAC-3' (SEQ ID NO: 22).

As an avidin which is a component of HLA tetramer, any avidin heretofore known can be used. However, it is preferred that said avidin is labeled with fluorescence to facilitate the detection by flow cytometry or fluorescent microscopy, and the like. Any known fluorescent pigments can be used without limitation, for example, phycoerythrin (PE), fluorescein isothiocyanate (FITC), peridinyl chlorophyll protein (PerCP), allophycocyanin (APC), phycoerythrin-texasred (also called ECD), and phycoerythrin-cyanine 5.1 (also called PC5), or the like.

The process for the preparation of HLA tetramers comprising those components for an HLA tetramer is well known as described in literatures (Science 279: 2103-2106 (1998), Science 274: 94-96 (1996), etc. The preparation will be hereinafter described briefly.

First, an appropriate host cells such as E. coli or mammalian cells capable of expressing a protein is transformed with an HLA α-chain expression vector and a β2-microglobulin expression vector, and allowed to express. E. coli (e.g., BL21) is preferably used here. The resultant monomer HLA complex and an antigen peptide (WT1-derived cancer antigen peptide) are then mixed to form a soluble HLA-peptide complex. The C-terminal sequence of HLA α-chain of the resultant HLA-peptide complex is biotinylated with BirA enzyme. When a biotinylated HLA-peptide complex and a fluorescently labeled avidin are mixed at the molar ratio of 4:1, an HLA tetramer is formed. It is preferred to purify the resulting protein by gel filtration or the like in each step above.

The step (b) above is carried out by bringing an HLA tetramer prepared as mentioned above into contact with a biological sample (a biological sample containing CTL precursors isolated from a test subject). The contact is preferably carried out at 37° C. Furthermore, the contact is preferably carried out in a normal biological buffer such as phosphate buffer containing serum (PBS).

It is preferred that a negative control is prepared by conducting the same procedures in parallel using fluorescently labeled streptavidin in stead of HLA tetramer.

In step (c) after step (b), the existence frequency or amount of WT1-specific CTL precursor cells bound to an HLA tetramer is measured. The measurement can be carried out by any of heretofore known methods. When an HLA tetramer is fluorescently labeled, CTL precursor cells bound to the HLA tetramer are also labeled with fluorescein. The so labeled CTLs can be detected or isolated by flow cytometry or fluorescent microscopy.

The existence frequency of WT1-specific CTL precursor cells bound to HLA tetramer can be obtained by, for example, measuring the proportion (frequency) of HLA tetramer-bound cells among CD8-positive cells (CD8-positive CTL precursor cell) or CD8/CD3-positive cells (CD8/CD3-positive CTL precursor cells).

The CD8-positive cells can be labeled and detected using, for example, fluorescently labeled mouse anti-human CD8 monoclonal antibody. The CD3-positive cells can be labeled and detected using, for example, fluorescently labeled mouse anti-human CD3 monoclonal antibody.

A fluorescent pigment used here must be different from that used in the HLA tetramer. That is, fluorescent pigments distinct from each other must be used, for example, when PE-labeled HLA tetramer is used, FITC-labeled mouse anti-human CD8 monoclonal antibody and PerCP-labeled mouse anti-human CD3 monoclonal antibody are usable.

The concrete process comprises, when the proportion (frequency) of HLA tetramer-bound cells for CD8-positive cells is measured, for example, bringing PE-labeled HLA tetramer contact with a biological sample, adding FITC-labeled mouse anti-human CD8 monoclonal antibody, allowing to react the mixture, and analyzing the stained cells by flow cytometry or fluorescent microscopy. The CD8-positive cells (CD8$^+$) are selected. The proportion (frequency) of CTL precursor cells specific for WT1 antigen peptide can be calculated by subtracting the proportion of avidin-positive cells (CD8$^+$avidin$^+$) as the negative control from the proportion of tetramer-positive cells (CD8$^+$ tetramer$^+$) in the selected CD8$^+$ cells, as follows:

WT1 antigen peptide-specific CTL precursor cells (%)=100×{[(CD8$^+$tetramer$^+$ cells)/(CD8$^+$ cells)]−[(CD8$^+$avidin$^+$ cells)/(CD8$^+$ cells)]}

When the proportion (frequency) of HLA tetramer-bound cells for CD8- and CD3-positive cells is measured, for example, bringing PE-labeled HLA tetramer contact with a biological sample, adding FITC-labeled mouse anti-human CD8 monoclonal antibody and PerCP-labeled mouse anti-human CD3 antibody, allowing to react the mixture, and analyzing the stained cells by flow cytometry or fluorescent microscopy. The CD3- and CD8-positive cells (CD3$^+$CD8$^+$) are selected. The proportion (frequency) of CTL precursor cells specific for WT1 antigen peptide can be calculated by subtracting the proportion of avidin-positive cells (CD3$^+$CD8$^+$avidin$^+$) as the negative control from the proportion of tetramer-positive cells (CD3$^+$CD8$^+$tetramer$^+$) in the selected CD3$^+$CD8$^+$ cells, as follows:

WT1 antigen peptide-specific CTL precursor cells (%)=100×{[(CD3$^+$CD8$^+$tetramer$^+$ cells)/(CD3$^+$CD8$^+$ cells)]−[(CD3$^+$CD8$^+$avidin$^+$ cells)/(CD3$^+$CD8$^+$ cells)]}

The responsiveness to WT1 vaccine is evaluated on the basis of the results obtained by the measurement above. Specifically, it can be carried out by comparing the existence frequency or amount of WT1-specific CTL precursor cells in a test subject obtained in step (b) (hereinafter, referred to as "test subject value") with that of healthy subject (hereinafter, referred to as "healthy subject value"), and deciding the difference between them. In this case, a biological material isolated and prepared from a healthy subject is needed (blood, lymph fluid, PBMC, etc.), which can be obtained by collecting a biological sample from a subject not having cancer. As used herein, "healthy subject" means a person who hare not diagnosed to have cancer.

The comparison between the test subject values and the healthy subject values can be carried out by measuring the biological sample of a test subject and that of a healthy subject in parallel. When the parallel comparison is not conducted, the comparison can also be carried out using a mean value or a statistical intermediate value of healthy subject values calculated from the healthy subject values obtained by measuring plural (at least two, preferably three or more, more preferably five or more) biological samples of a healthy subject under a constant conditions when the parallel measurement is not conducted.

The evaluation whether or not a test subject is highly responsive to WT1 vaccine can be carried out using as an indicator that the test subject value is 1.5 times or higher, preferably 2 times or higher compared to the healthy subject value. That is, when the test subject value is 1.5 times or higher, preferably, 2 times or higher than the healthy subject value, the responsiveness to WT1 vaccine is evaluated to be high. A patient evaluated to be highly responsive to WT1 vaccine is evaluated to be suitable for WT1 vaccine, in other words, it is possible to apply WT1 vaccine therapy to the patient preferably.

The method of selecting patients of the present invention as described above can also be used in not only the evaluation of patients before vaccine administration but also diagnosis or confirmation of efficacy after vaccine administration.

The present invention also provides a method of selecting a patient highly responsive to WT1 vaccine, which comprises the following steps (a), (b), and (c):

(a) isolating a biological sample containing CTL precursor cells from a test subject;

(b) measuring the existence frequency or amount of WT1-specific CTL precursor cells of effector type in the biological sample of (a); and (c) deciding whether or not the measured value of (b) is high by comparison with that of healthy subject, and evaluating the responsiveness to WT1 vaccine, and a method of treating cancer in the patient selected by said method.

The present inventor sorted WT1-specific CTL precursor cells finely regarding function, and found that, in particular, the effector-type CTL precursor cells exist in higher proportion compared to healthy individuals. Accordingly, patients highly responsive to WT1 vaccine can be selected on the basis of the amount or frequency of WT1-specific CTL precursor cells of effector type as an indicator. The method of selection which uses effector-type CTL precursor cells as an indicator can be useful to carry out more detailed analysis, when there are no/poor differences between the values of a test subject and those of a healthy subject when measured by the method of selection which uses the existence frequency or amount of CTL precursor cells as an indicator.

Specific example of a method of selection comprises the following steps (a), (b), (c) and (d):

(a) isolating a biological sample containing CTL precursor cells from a test subject;

(b) bringing an HLA tetramer comprising a WT1-derived tumor antigen peptide, an anti-CD8 antibody, an anti-CD45RA antibody and an anti-CD27 antibody contact with the biological sample of (a);

(c) measuring the proportion of CD45RA-postive and CD27-negative CTL precursor cells of effector type among CTL precursor cells which are positive for CD8 or CD8/CD3 and positive for binding to HLA tetramer; and (d) deciding whether or not the measured value of (c) is high by comparison with that of healthy subject, and evaluating the responsiveness to WT1 vaccine, and a method of treating cancer in the patient selected by said method.

As used herein, the term "effector cell" means CD45RA-positive and CD27-negative CTL precursor cell. The frequency of said effector cells can be obtained by measuring the proportion of CD45RA-positive and CD27-negative CTL precursor cell among CTL precursor cells. Specifically, it can be carried out by bringing a test sample into contact with an HLA tetramer, an anti-CD8 antibody, an anti-CD45RA antibody and an anti-CD27 antibody; and measuring the proportion of CD45RA-postive and CD27-negative cells among CTL precursor cells (WT1-specific CTL precursor cells) which are positive for CD8 or CD8/CD3 and positive for binding to HLA tetramer.

The CD45RA-positive cells can be labeled and detected using, for example, fluorescently labeled mouse anti-human CD45RA monoclonal antibody. The CD27-positive cells can be labeled and detected using, for example, fluorescently labeled mouse anti-human CD27 monoclonal antibody. A fluorescent pigment used here must be different from that used in the HLA tetramer, anti-CD8 antibody or anti-CD3 antibody. That is, fluorescent pigments distinct from each other must be used, for example, when PE-labeled HLA tetramer, FITC-labeled anti-CD8 monoclonal antibody and Per-labeled anti-CD3 monoclonal antibody are used, ECD-labeled mouse anti-human CD45RA monoclonal antibody and PC5-labeled mouse anti-human CD27 monoclonal antibody are usable. Those labeled antibodies can be purchased from Beckman Coulter, and the like.

The concrete process for measuring the precursor cells or the like can be carried out in a similar manner to the method of selection described above wherein the existence frequency or amount of CTL precursor cells is used as an indicator.

The method of selecting patients highly responsive to WT1 vaccine as described above is also applicable to diagnosis of cancer. That is, the present inventor found that the frequency of WT1-specific CTL precursor cells is higher in patients of hematopoietic malignancy or lung cancer compared to healthy individuals. Accordingly, it is possible to diagnose cancer using the frequency of WT1-specific CTL precursor cells or WT1-specific CTL precursor cells of effector type as an indicator. Examples of cancer that can be diagnosed include blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer. Preferred examples are leukemia, myelodysplastic syndrome and lung cancer.

The present invention also provides a method of identifing a target molecule of WT1 vaccine said molecule being peculiar to a patient, comprising the following steps (a), (b), (c) and (d):

(a) isolating a biological sample containing CTL precursor cells from a test patient;

(b) applying each of plural target molecules of WT1 vaccine to the biological sample of (a);

(c) measuring the existence frequency or amount of WT1-specific CTL precursor cells in the respective biological samples of (b) and comparing the results with each other; and (d) identifying a target molecule of WT1 vaccine effective to the test patient on the basis of the results obtained in (c).

The present inventor has found that there exist WT1-specific CTL precursor cells in a patient before vaccine administration in high frequency than that hitherto known. Accordingly, it is possible to identify a target molecule (target molecule for therapeutic use) of WT1 vaccine said molecule being peculiar to a patient on the basis of the amount or frequency of WT1-specific CTL precursor cells as an indicator.

That is, the identification method above can be used effectively to identify the most suitable target molecule (antigen peptide) for treating a patient who has been evaluated to be highly responsive to WT1 vaccine.

Specifically, the identification can be carried out, similarly to the method of selecting patients highly responsive to WT1 vaccine, by measuring the existence frequency or amount of WT1 specific CTL precursor cell using HLA monomer method, HLA dimer method, HLA tetramer method, HLA pentamer method, ELISPOT method, realtime RT-PCR technique or limiting dilution method. Preferably, HLA monomer method, HLA dimer method, HLA tetramer method or HLA pentamer method is used. The method of identification will be hereinafter described concretely taking the HLA tetramer method as an example.

The method involving HLA tetramer method comprises the following steps (a), (b), (c) and (d):

(a) isolating a biological sample containing CTL precursor cells from a test patient;

(b) bringing each of plural HLA tetramers comprising different WT1-derived tumor antigen peptides contact with the biological sample of (a);

(c) measuring the existence frequency or amount of WT1-specific CTL precursor cells bound to the respective HLA tetramers, and comparing the results with each other; and (d) identifying WT1-derived tumor antigen peptide effective to the test patient on the basis of the results obtained in (c).

Specifically, plural HLA tetramers each containing a WT1-derived cancer antigen peptide as a candidate are prepared. Then each of the HLA tetramer is brought into contact with a biological sample isolated from a test patient, and the existence frequency or amount of WT1-specific CTL precursor cells bound to an HLA tetramer is measured. The values obtained from respective HLA tetramers are compared and a cancer antigen peptide comprised in the HLA tetramer that showed the highest value, which is a cancer antigen peptide that is most readily recognized by CTLs, is identified as the target molecule for WT1 vaccine therapy for the patient, i.e., the target molecule peculiar to the patient.

Any cancer antigen peptide can be used as far as it is derived from WT1, and examples include cancer antigen peptides set forth in SEQ ID NOs: 2 to 18. Preferred cancer antigen peptide is the one set forth in any one of SEQ ID NOs: 2-5.

The concrete process of respective steps or method of preparation for each component can be found in the above section regarding a method of selecting a patient highly responsive to WT1 vaccine.

According to the present method of identifying a target molecule of WT1 vaccine, it is possible to identify a target molecule capable of treating cancer peculiar to a patient. Therefore, in a different embodiment, the present invention provides a pharmaceutical composition for treating cancer in a given patient, which comprises a target molecule identified by the method of identification of a target molecule of WT1 vaccine said molecule being peculiar to the patient; and a method of treatment of cancer peculiar to a patient, which comprises administering to the patient the target molecule identified by the method of identification. The pharmaceutical composition of the present invention comprises cancer vaccine and may contain an adjuvant and the like which are known in the art.

The present invention further provides a clinical diagnostic agent for selecting a patient highly responsive to WT1 vaccine, which comprises as an ingredient an HLA monomer, an HLA dimer, an HLA tetramer or an HLA pentamer each containing a WT1-derived tumor antigen peptide. The clinical diagnostic agent of the present invention will be hereinafter described taking HLA tetramer as an example.

The "HLA tetramer" as an ingredient of the clinical diagnostic agent of the present invention refers to, as mentioned above, a tetramer prepared by biotinylating a complex (HLA monomer) obtained by association of an HLA antigen α-chain and a β2-microglobulin with a WT1-derived cancer antigen peptide, and allowing to bind to avidin for tetramerization (Science 279: 2103-2106 (1998); and Science 274: 94-96 (1996)).

Any cancer antigen peptide can be used here as far as it is derived from WT1, and examples include cancer antigen peptides set forth in SEQ ID NOs: 2 to 18. Preferred cancer antigen peptide is the one set forth in any one of SEQ ID NOs: 2-5.

The process of respective steps or method of preparation for each component can be found in the above section regarding the method of selecting a patient highly responsive to WT1 vaccine.

The clinical diagnostic agent of the present invention can be a component of a kit for selecting a patient highly responsive to WT1 vaccine. The kit may be the one that is composed of a clinical diagnostic agent alone of the present invention or the one that is composed of a clinical diagnostic agent of the present invention and other ingredient(s). Examples of other ingredients in the kit include fluorescently labeled streptavidin, fluorescently labeled mouse anti-human CD8 monoclonal antibody, fluorescently labeled mouse anti-human CD3 monoclonal antibody, and the like. When effector cells are detected, the kit may contain fluorescently labeled mouse anti-human CD45RA monoclonal antibody, fluorescently labeled mouse anti-human CD27 monoclonal antibody.

Examples of fluorescent pigment include phycoerythrin (PE), fluorescein isothiocyanate (FITC), peridinyl chlorophyll protein (PerCP), allophycocyanin (APC), phycoerythrin-texasred (also called ECD), and phycoerythrin-cyanine 5.1 (also called PC5), and the like.

The clinical diagnostic agent and a kit of the present invention can be used in the selection not only a patient highly responsive to WT1 vaccine but also a target molecule of WT1 vaccine (target molecule for treatment). In addition, the agent can be used as a diagnostic agent for cancer without changing the components.

The present invention also provides a method of determining the suitability of a patient for WT1 vaccine, comprising the following steps (a), (b) and (c):

(a) isolating a biological sample containing CTLs from a patient after WT1 vaccine administration;

(b) measuring the existence frequency or amount of WT1-specific CTLs in the biological sample of (a);

(c) deciding whether or not the measured value of (b) is high by comparison with that of biological sample obtained before WT1 vaccine administration, and evaluating whether the patient is suitable for WT1 vaccine therapy, and a method of treating cancer in a patient, which comprises treating the patient evaluated to be suitable by the method of determination with WT1 or WT1-derived cancer antigen peptide.

As described in the Examples below, the present inventor measured the frequency of WT1-specific CTLs in patients undergoing treatment with a WT1-derived tumor antigen peptide ("WT1 vaccine") and found that the therapeutic effect is correlated with the increase of CTL frequency after administration of the peptide relative to that obtained before administration thereof. That is, the case where the existence frequency of WT1-specific CTLs after administration of WT1 peptide is 1.5 times or higher compared to that in the sample obtained before administration is defined as "positive immune response", and the relationship between the immunoresponsiveness and the therapeutic effect was investigated. As a result, positive correlation was recognized between the immunoresponsiveness and the therapeutic effect. This result revealed that it is possible to evaluate whether or not treatment with WT1 vaccine is suitable for a subject patient on the basis of the above-mentioned immunoresponsiveness (increase in the frequency or amount of CTLs) as an indicator.

Thus, the method of determination of the present invention can be used effectively to evaluate the suitability of treatment for a patient undergoing WT1 vaccine therapy, for example, the suitability of continuous treatment with peptide administration.

The concrete procedures in the steps (a) and (b) of the method of determination can be found in the above section regarding the "method of selecting a patient highly responsive to WT1 vaccine". Specifically, it can be carried out by measuring the existence frequency or amount of WT1-specific CTLs by HLA monomer method, HLA dimer method, HLA tetramer method, HLA pentamer method, ELISPOT method, realtime RT-PCR technique, limiting dilution method, or the like.

The evaluation whether or not a patient is suitable for WT1 vaccine therapy in the step (c) is carried out by comparing the existence frequency or amount of WT1-specific CTLs obtained from the patient after administration of WT1 vaccine (hereinafter, referred to as "post-administration value") and that obtained before administration of WT1 vaccine (hereinafter, referred to as "pre-administration value"), and deciding the difference between the both values.

As used herein, "after administration of vaccine" refers to any time (timing) after one or more times of WT1 vaccine administration. However, in the case of peptide-dosing schedule of two-week-interval, preferred time (timing) is after the first to fifth WT1 vaccine administration, preferably, after the first to third WT1 vaccine administration.

The evaluation whether or not treatment with WT1 vaccine is suitable can be carried out using as an indicator that the post-administration value is 1.5 times or higher compared to the pre-administration value. That is, when the post-administration value is 1.5 times or higher than the pre-administration value, treatment with WT1 vaccine is evaluated to be suitable. On the basis of these findings, the present invention also provides a method of treating cancer in a patient, which comprises treating a patient who has been evaluated to be suitable by the method of determining the suitability of a patient for WT1 vaccine of the present invention with WT1 or WT1-derived tumor antigen peptide.

Among the above-mentioned methods of measuring CTL, the HLA monomer method, HLA dimer method, HLA tetramer method and HLA pentamer method are principally preferred from the viewpoint of easiness of handling and accuracy. The method of determination will be hereinafter described taking the HLA tetramer method as an example, The method involving HLA tetramer method comprises the following steps (a), (b), (c) and (d):

(a) isolating a biological sample containing CTLs from a patient after WT1 vaccine administration;

(b) bringing an HLA tetramer comprising a WT1-derived tumor antigen peptide contact with the biological sample of (a);

(c) measuring the existence frequency or amount of WT1-specific CTLs bound to the HLA tetramer; and (d) deciding whether or not the measured value of (c) is high by comparison with that of biological sample obtained before WT1 vaccine administration, and evaluating whether the patient is suitable for WT1 vaccine therapy.

The HLA antigen used here as a component of HLA tetramer includes an HLA-A24 antigen or an HLA-A2 antigen.

Examples of cancer antigen peptide as a component of an HLA tetramer include: Cys Met Thr Trp Asn Gln Met Asn Leu (SEQ ID NO: 2), Cys Tyr Thr Trp Asn Gln Met Asn Leu (SEQ ID NO: 3), Arg Met Phe Pro Asn Ala Pro Tyr Leu (SEQ ID NO: 4) and Arg Tyr Pro Ser Cys Gln Lys Lys Phe (SEQ ID NO: 5). As all the peptides set forth in SEQ ID NO: 2-5 are peptides capable of binding to HLA-A24, examples of HLA tetramer used in the above-mentioned method for determination of the present invention includes HLA tetramers comprising any one of peptides set forth in SEQ ID NO: 2-5 and an HLA-A24 antigen. In addition, as the peptides set forth in SEQ ID NO: 2 and 4 are also capable of binding to HLA-A2 antigen, HLA tetramers comprising a peptide set forth in SEQ ID NO: 2 or 4 and an HLA-A2 antigen are also included.

In the method of determination or treatment of the present invention, it is preferred to use an HLA tetramer comprising the same peptide as that used in the treatment or a peptide with which CTLs show cross-reaction, said CTLs having been induced by the peptide used in the treatment. For example, when a peptide set forth in SEQ ID NO: 3 is used in the treatment of a patient, an HLA tetramer comprising a peptide set forth in SEQ ID NO: 2 or 3 and an HLA-A24 antigen is used effectively.

The concrete procedures in the steps (a) to (c) of the method of determination or treatment of the present invention can be found in the above section regarding the "method of selecting a patient highly responsive to WT1 vaccine". Further, the evaluation of step (d) can be carried out on the basis of the comparison of pre-administration values and post-administration values as mentioned above.

The specific example of the method of determination or treatment of the present invention will be hereinafter described.

First, blood is collected from a patient having cancer before administration of WT1-derived cancer antigen peptide, and PBMC is separated (pre-administration sample). Then, blood is collected from the patient after treated by peptide administration, and PBMC is separated (post-administration sample). To respective pre- and post-administration samples are added an HLA tetramer, and the frequency of peptide-specific CTLs is measured and calculated according to the methods of analysis which are described in the above section regarding the "method of selecting a patient highly responsive to WT1 vaccine" and Example 3. When the CTL frequency in the post-administration sample is 1.5 times or higher compared to that of pre-administration sample, it is evaluated that treatment with WT1 vaccine is suitable (i.e., WT1 vaccine is expected to be therapeutically effective).

The present invention also provides a clinical diagnostic agent for determining the suitability for WT1 vaccine which comprises as an ingredient an HLA monomer, an HLA dimer, an HLA tetramer or an HLA pentamer each containing a WT1-derived cancer antigen peptide, and a kit comprising said clinical diagnostic agent. The ingredients of said clinical diagnostic agent and kit are as defined in the above section regarding the "diagnostic clinical agent for the selection of a patient highly responsive to WT1 vaccine".

EXAMPLES

The present invention is further illustrated by the following examples, but is not limited by these examples in any respect.

Example 1

Preparation of Peripheral Blood Mononuclear Cells

After obtaining informed-consent, blood was collected from HLA-A*2402-positive patients having cancer and HLA-A*2402-positive healthy individuals. Among patients, those having hematopoietic malignant tumor were eighteen which composed of acute myelocytic leukemia (AML) (n=11), acute lymphatic leukemia (ALL) (n=2), chronic myelocytic leukemia (CML) (n=1), and myelodysplastic syndrome (MDS) (n=4); and those having lung cancer were seven. There were ten HLA-A*2402-positive healthy individuals.

As for the patients having hematopoietic malignant tumor, significant high expression of WT1 gene was identified in myeloma and peripheral blood samples once or more at the time of diagnosis or in the course of treatment. As for the patients having lung cancer, significant high expression of WT1 gene was identified in biopsy or extracted samples.

Peripheral mononuclear cells (PBMCs) were separated from the collected blood by density gradient centrifugation method (Ficoll-Hypaque) and stored in liquid nitrogen in frozen state.

Example 2

Preparation of HLA Tetramer

A tetramer comprising HLA-A*2402 labeled with fluorescent pigment (Phycoerythrin; PE) was prepared using a 9-amino-acid peptide (SEQ ID NO: 2) comprising the amino acid sequence at position 235-243 of WT1 protein according to the method described in Int. J. Cancer: 100, 565-570, 2002.

First, cDNA encoding recombinant HLA-A2402 was amplified by PCR using an HLA-A*2402 expression plasmid (GenBank Acc. No. M64740) as a template and a forward primer: 5'-CCATGGGCAGCCATTCTATGCGCT-ATTTTTCTACCTCCGT-3'(SEQ ID NO: 19); and a reverse primer: 5'-GGATCCTGGCTCCCATCTCAGGGT-GAGGGGCTTGGGCAGACCCTC-3'(SEQ ID NO: 20).

The reverse primer encodes a B irA recognition sequence so that the frames conforms at the c-terminus. The amplified fragments were cleaved by restriction enzymes NcoI and BamH1, and cloned into pET11d vector (Novagen).

Then cDNA encoding recombinant soluble human β2 microglobulin was amplified using a human β2-microglobulin expression plasmid (GenBank Acc. No. ABO21288) as a template and a forward primer: 5'-CATATGATCCAGCG-TACCCCGAAAATTCAG-3' (SEQ ID NO: 21); and a reverse primer: 5'-GGATCCTTACATGTCTCGATC-CCACTTAAC-3' (SEQ ID NO: 22).

The amplified fragments were cleaved by restriction enzymes NdeI and BamH1, and cloned into pET11a vector (Novagen).

The resulting two vectors were allowed to express in *E. coli*. BL21, and recovered as insoluble fractions of inclusion bodies. The respective inclusion bodies were dissolved in 8M urea solution and diluted by a refolding buffer. To the dilution was added a peptide (SEQ ID NO: 2) to form a soluble HLA-peptide complex. The C-terminal sequence of the HLA-peptide complex was biotinylated with Bir A enzyme and the resulting biotinylated HLA-peptide tetramer was purified by gel filtration technique. The biotinylated HLA-peptide complex and PE-labeled avidin (Molecular Probe) were mixed at molar ratio of 4:1 to prepare HLA tetramer.

Example 3

Analysis of WT1-Specific CTL Precursor Cells with HLA Tetramer

The frozen PBMCs obtained in Example 1 were thawed, and immediately re-suspended in a phosphate buffered saline (PBS) containing 0.5% fetal bovine serum (FCS) at the cell density of $1\times10^6$ cells/ml. To the suspension was added a solution of tetramer (500 µg/µl, 2 µl) prepared in Example 2. The suspension was then incubated at 37° C. for 30 minutes. A sample for the negative control was prepared by treating in a similar manner except that PE-labeled streptavidin (Becton Dickinson) was added instead of tetramer. After quenching with ice-cooled water, FITC-labeled mouse anti-human CD8 monoclonal antibody (15 µl, BD Pharmigen) and PerCP-labeled mouse anti-human CD3 antibody (15 µl, BD Pharmigen) were added, and the mixture was incubated at 4° C. for 30 minutes. The stained cells were subjected to centrifugal washing with PBS containing 0.5% FCS (2×), and analyzed by flow cytometer FACSort (Becton Dickinson). CD3- and CD8-positive cells ($CD3^+CD8^+$) were selected. The proportion of WT1-antigen peptide specific CTL precursor cells was calculated by subtracting the proportion of PE-labeled streptavidin-positive cells ($CD3^+CD8^+avidin^+$) in the negative control from the proportion of tetramer-positive cells ($CD3^+CD8^+tetramer^+$) in the selected $CD3^+CD8^+$ cells, as follows:

WT1 antigen peptide-specific CTL precursor cells
(%)=100×{[($CD3^+CD8^+tetramer^+$ cells)/($CD3^+CD8^+$ cells)]−{[($CD3^+CD8^+avidin^+$ cells)/($CD3^+CD8^+$ cells)]}

The results of analysis of PBMCs of patients having cancer and healthy individuals are shown in Table 2. The results were plotted for respective diseases as shown in FIG. 1. These results showed that the proportion of WT1 antigen peptide-specific CTL precursor cells in CD3/CD8-positive cells was 0.47 to 1.30% (average=0.82%) for healthy individuals, 1.04-29.45% (average=5.24%) for patients having malignant hematopoietic tumor, and 0.33-5.97% (average=2.44%) for patients having lung cancer. The statistical analysis revealed that the proportion was significantly increased (p<0.05) in patients having malignant hematopoietic tumor or lung cancer compared to healthy individuals.

TABLE 2

| Sample, patient No. | Frequency of CTL precursors (%) |
|---|---|
| AML, patient No. 1 | 8.26 |
| AML, patient No. 2 | 8.01 |
| AML, patient No. 3 | 5.12 |
| AML, patient No. 4 | 3.84 |
| AML, patient No. 5 | 4.51 |
| AML, patient No. 6 | 3.27 |
| AML, patient No. 7 | 2.68 |
| AML, patient No. 8 | 2.60 |
| AML, patient No. 9 | 1.77 |
| AML, patient No. 10 | 1.04 |
| AML, patient No. 11 | 1.49 |
| ALL, patient No. 1 | 7.32 |
| ALL, patient No. 2 | 1.78 |
| CML, patient 1 | 2.46 |
| MDS, patient 1 | 29.45 |
| MDS, patient 2 | 2.99 |
| MDS, patient 3 | 2.81 |
| MDS,. patient 4 | 2.08 |
| lung cancer. patient 1 | 5.97 |
| lung cancer. patient 2 | 3.83 |
| lung cancer. patient 3 | 2.63 |
| lung cancer. patient 4 | 1.89 |
| lung cancer. patient 5 | 1.69 |
| lung cancer. patient 6 | 0.72 |
| lung cancer. patient 7 | 0.33 |
| healthy individual 1 | 1.30 |
| healthy individual 2 | 1.05 |
| healthy individual 3 | 1.08 |
| healthy individual 4 | 0.85 |
| healthy individual 5 | 0.81 |
| healthy individual 6 | 0.79 |
| healthy individual 7 | 0.61 |
| healthy individual 8 | 0.64 |
| healthy individual 9 | 0.57 |
| healthy individual 10 | 0.47 |

AML: acute myelocytic leukemia
ALL: acute lymphatic leukemia
CML: chronic myelocytic leukemia
MDS: myelodysplastic syndrome

Example 4

Analysis of Frequency of WT1-Specific CTLs After Pentide Administration

The following test was carried out after obtaining approval of ethical committee of Osaka University, Faculty of Medicine, and informed consent of cancer patients.

A peptide comprising the amino acid sequence at position 235-243 of WT1 (SEQ ID NO:2) or its variant comprising SEQ ID NO: 3 wherein the methionine at position 2 of SEQ ID NO: 2 is replaced by tyrosine was administered to cancer patients at 0.3 mg, 1 mg or 3 mg per body. The peptide was emulsified with Montanide ISA51 (SEPPIC), and the resulting emulsion was intradermally injected once or plural times at 2-week-intervals. Subject patients were suffering from HLA-A*2402-positive and WT1-positive lung cancer, breast cancer or leukemia.

The immune response to the administered peptide was evaluated on the basis of the CTL frequency measured by the HLA tetramer method similar to Example 3. When the frequency of peptide-specific CTLs at any stage after peptide administration is increased by 1.5 times or higher compared to that obtained before peptide administration, it was evaluated to be "positive immune response". Further, when the tumor marker values, the number of tumor cells or the volume of tumor decreased, it was evaluated to be "therapeutically effective". The correlation between the immune response and therapeutic effect was evaluated by chi-square test in cancer patients (n=19) who have been evaluated for the immune response to and therapeutic effect of peptide administration. As a result, eight (73%) of eleven patients who were positive regarding therapeutic effect showed positive immune response, while only two (25%) of eight patients who were negative regarding therapeutic effect showed positive immune response, indicating that the therapeutic effect and the immune response are positively correlated (P=0.0397). These results indicates that the induction of CTLs specific for the administered peptide is an important factor for the therapeutic effect. In addition, the immunoresponsiveness above can be used as an indicator for the conformation of favorable progress of treatment with peptide administration or the decision whether or not treatment by the peptide administration should be continued.

Example 5

Analysis of Function of WT1-Specific CTLs

It has been reported that antigen-peptide specific CTLs positive for the HLA tetramer staining and CD8 can be further sorted finely by staining with anti-CD45RA antibody and anti-CD27 antibody (J. Exp. Med., 186, p 1407, 1997). The CD45RA-positive and CD27-positive cells are classified into naive type; CD45RA-negative and CD27-positive, and CD45RA-negative and CD27-negative cells into memory type; and CD45RA-positive and CD27-negative cells into effector type. The effector-type cells represent cell populations of the strongest CTL activity.

PBMCs were collected before peptide administration from HLA-A*2402-positive cancer patients (n=24; 14 blood cancers, 10 solid cancers) who were tested by the clinical research in Example 4 and HLA-A*2402-positive healthy individuals after obtaining informed consent. The PMBCs were used in the analysis of function of WT1-peptide specific CTL precursors which are positive for the HLA tetramer staining and CD8. For the analysis by flow cytometry, cells were stained in a similar manner to Example 3 with HLA tetramer, anti-CD8 antibody, anti-CD45RA antibody, and anti-CD27 antibody. The proportion of cells belonging to CD45RA-positive/CD27-positive naive type, CD45RA-negative memory type or CD45RA-positive/CD27-negative effector type in HLA tetramer-positive and CD8-positive cell populations was calculated. The proportions for naive-type, memory-type and effector-type cells were 23.7%, 45.5% and 30.8% for the cancer patients. As for healthy individuals, the proportions were 35.9%, 53.8% and 8.9%. The comparison of cancer patients and healthy individuals showed that the proportion of effector-type cells is significantly high (P<0.05) in the cancer patients; however, there are no significant differences between the cancer patients and healthy individuals regarding the proportion of naive-type and memory-type cells. In Example 3, the cancer patients showed increase of WT1-specific CTL precursor cells, and, now the cancer patients revealed to show increase of proportion of CTLs having effector-type function among CTLs. These results demonstrated that the cancer patients can be diagnosed on the basis of the existence frequency of effector type CTL precursor cells.

INDUSTRIAL APPLICABILITY

According to the present invention, a method of selecting a patient highly responsive to WT1 vaccine on the basis of existence frequency of WT1-specific C T L precursor cells as an indicator, a method of treating cancer utilizing the same, and clinical diagnostic agents for the selection, and the like, are provided. According to the method of selection of the present invention, a patient who is expected to be responsive to WT1 vaccine therapy can be selected, which makes it possible to treat cancer more appropriately.

The invention claimed is:

1. A method of selecting a cancer patient highly responsive to WT1 vaccine and treating the patient, comprising:
   (a) isolating PBMCs or blood containing CTL precursor cells from a cancer patient who has not been previously immunized with WT1 vaccine;
   (b) contacting the PBMCs or blood of (a) with an HLA tetramer comprising a peptide, wherein the HLA tetramer is an HLA-A2 tetramer comprising a peptide comprising the amino acid sequence of SEQ ID NO: 4, or an HLA-A24 tetramer comprising a peptide comprising the amino acid sequence of SEQ ID NO: 2 or 3,
   (c) determining the number of $CD8^+CD45RA^+CD27^-$ CTL precursor cells bound to any one of the HLA tetramers relative to the number of $CD8^+$ CTL precursor cells bound to the same HLA tetramer, and
   (d) administering a WT1 vaccine to a cancer patient who has a ratio of $CD8^+CD45RA^+CD27^-$ to $CD8^+$ cells as determined in (c) that is significantly higher, as defined by a p value of <0.05, than the ratio of $CD8^+CD45RA^+CD27^-$ CTL precursor cells to $CD8^+$ CTL precursor cells which bind the same tetramer as in (c) contained within the PBMCs or blood of a control subject who does not have cancer,
   wherein the WT1 vaccine comprises at least one WT1-derived cancer antigen peptide selected from the group consisting of:

```
                                                  (SEQ ID NO: 2)
Cys Met Thr Trp Asn Gln Met Asn Leu, (SEQ ID NO: 3)
Cys Tyr Thr Trp Asn Gln Met Asn Leu,
and (SEQ ID NO: 4)
Arg Met Phe Pro Asn Ala Pro Tyr Leu.
```

2. The method of claim 1, wherein the cancer patient has leukemia, myelodysplastic syndrome, multiple myeloma, malignant lymphoma or another hematopoietic malignancy.

3. The method of claim 1, wherein the cancer patient has lung cancer or another solid cancer.

4. The method of claim 1, wherein the biological sample is blood.

5. The method of claim 1, wherein the biological sample comprises PBMCs isolated from blood.

6. The method of claim 1, wherein the HLA tetramer is the HLA-A2 tetramer comprising the peptide comprising the amino acid sequence of SEQ ID NO: 4.

7. The method of claim 1, wherein the HLA tetramer is the HLA-A2 tetramer comprising the peptide comprising the amino acid sequence of SEQ ID NO: 2 or 3.

8. The method of claim 1, wherein (c) comprises:
   contacting the PBMCs or blood with the HLA tetramer and with an anti-CD8 antibody, an anti-CD45RA antibody, and an anti-CD27 antibody,
   detecting the number of $CD8^+CD45RA^+CD27^-$ CTL precursor cells bound to the HLA tetramer, and
   detecting the number of $CD8^+$ CTL precursor cells bound to the HLA tetramer.

9. The method of claim 1, wherein (c) comprises flow cytometry.

10. The method of claim 1, wherein in (d) the ratio of $CD8^+CD45RA^+CD27^-$ CTL precursor cells bound to the HLA tetramer in the cancer patient is 1.5 times or higher than the ratio of HLA tetramer-binding $CD8^+CD45RA^+CD27^-$ CTL precursor cells from the control subject who does not have cancer.

11. The method of claim 1, wherein in (d) the ratio of $CD8^+CD45RA^+CD27^-$ CTL precursor cells bound to the HLA tetramer in the cancer patient is 2.0 times or higher than the ratio of HLA tetramer-binding $CD8^+CD45RA^+CD27^-$ CTL precursor cells from the control subject who does not have cancer.

12. A method of selecting a cancer patient highly responsive to a WT1 vaccine and treating the selected patient, comprising:
   (a) isolating a PBMCs or blood comprising CTL precursor cells from a cancer patient who has not been previously immunized with a WT1 vaccine;
   (b) contacting the PBMCs or blood of (a) with an HLA tetramer comprising a peptide, wherein the HLA tetramer is an HLA-A2 tetramer comprising a peptide comprising the amino acid sequence of SEQ ID NO: 4, or an HLA-A24 tetramer comprising a peptide comprising the amino acid sequence of SEQ ID NO: 2 or 3,
   (c) determining the number of $CD8^+CD45RA^+CD27^-$ CTL precursor cells bound to any one of the HLA tetramers relative to the number of $CD8^+$ CTL precursor cells bound to the same HLA tetramer,
   wherein the determining in (c) comprises:
   contacting the PBMCs or blood with the HLA tetramer and with an anti-CD8 antibody, an anti-CD45RA antibody, and an anti-CD27 antibody, and
   (d) identifying a cancer patient who has a ratio of $CD8^+CD45RA^+CD27^-$ to $CD8^+$ cells as determined in (c) that is significantly higher, as defined by a p value of <0.05, than the ratio of $CD8^+CD45RA^+CD27^-$ CTL precursor cells to CD8+ CTL precursor cells which bind the same tetramer as in (c) contained within the PBMCs or blood of a control subject who does not have cancer, and
   administering the WT1 vaccine to the identified cancer patient,
   wherein the WT1 vaccine comprises at least one WT1-derived cancer antigen peptide selected from the group consisting of:

```
                                                  (SEQ ID NO: 2)
Cys Met Thr Trp Asn Gln Met Asn Leu, (SEQ ID NO: 3)
Cys Tyr Thr Trp Asn Gln Met Asn Leu,
and (SEQ ID NO: 4)
Arg Met Phe Pro Asn Ala Pro Tyr Leu.
```

13. The method of claim 1, wherein
the cancer is hematopoietic malignancies, lung cancer, or breast cancer;
the HLA tetramer is the HLA-A24 tetramer comprising the peptide comprising the amino acid sequence of SEQ ID NO: 2 or 3; and
the WT1 vaccine comprises at least the WT1-derived cancer antigen peptide of SEQ ID NO: 2 or 3.

14. The method of claim 12, wherein
the cancer is hematopoietic malignancies, lung cancer, or breast cancer;
the HLA tetramer is the HLA-A24 tetramer comprising the peptide comprising the amino acid sequence of SEQ ID NO: 2 or 3; and
the WT1 vaccine comprises at least the WT1-derived cancer antigen peptide of SEQ ID NO: 2 or 3.

15. The method of claim 13, wherein
the cancer is acute myelocytic leukemia (AML), acute lymphatic leukemia (ALL), chronic myelocytic leukemia (CML), myelodysplastic syndrome (MDS), lung cancer, or breast cancer.

16. The method of claim 14, wherein
the cancer is acute myelocytic leukemia (AML), acute lymphatic leukemia (ALL), chronic myelocytic leukemia (CML), myelodysplastic syndrome (MDS), lung cancer, or breast cancer.

* * * * *